United States Patent [19]

Thornton et al.

[11] Patent Number: 5,498,414
[45] Date of Patent: Mar. 12, 1996

[54] **ATTENUATED STRAINS OF *AEROMONAS SALMONICIDA* USEFUL AS FISH VACCINES**

[75] Inventors: Julian C. Thornton, Brentwood Bay; William W. Kay, Victoria, both of Canada

[73] Assignee: University of Victoria, Victoria, Canada

[21] Appl. No.: 957,531

[22] Filed: Oct. 5, 1992

[51] Int. Cl.$^6$ .................. A61K 39/02; C12N 1/36; C12N 1/20
[52] U.S. Cl. ............... 424/234.1; 424/827; 435/243; 435/245; 435/252.1
[58] Field of Search .................. 424/92, 234.1, 424/827; 435/243, 252.1, 245

[56] References Cited

FOREIGN PATENT DOCUMENTS

WO89/09616  10/1989  WIPO.
WO91/13978  3/1991  WIPO.

OTHER PUBLICATIONS

Thornton et al, Microbial Pathogenesis 11: 85–99, 1991.
Cipriano, R. C., et al, "Immunization of Salmonids Against the Fish Pathogen *Aeromonas salmonicida*", J. World Maricul. Soc 14:201–211 1983.
Udey et al, Marine Fisheries Review, 40:12–17, 1978.
Hackett et al, Can J. Fish Quat Sci, 41(9):1354–1360, 1984.
Oliver et al, J. Aquatic Animal Health 2:119–127, 1990.
Sakai et al, Infect Immun 48(1):146–152, 1985.
Chapman et al, J. Wildlife Diseases 27(1):61–67, 1991.
McCarthy et al, Aquatic Microbiology SAB Symposium 6:229–324 1977.
Belland et al, J. Bacteriol 163(3):877–881, 1985.
Cipriano et al., "Immersion and Injection Vaccination of Salmonids Against Furunculosis with an Avirulent Strain of *Aeromonas salmonicida*," Prog. Fish–Cult. 44(4) (Oct. 1982).
Ellis et al., "Lack of relationship between virulence of *Aeromonas salmonicida* and the putative virulence factors: A–layer, extracellular proteases and extracellular haemolysins," J. of Fish Diseases 11:309–323 (1988).
Evenberg et al., "Biochemical and immunological characterization of the cell surface of the fish pathogenic bacterium *Aeromonas salmonicida*," Biochimica et Biophysica Acta 815:233–244 (1985).
Griffiths and Lynch, "Characterization of *Aeromonas salmonicida* Mutants with Low–Level Resistance to Multiple Antibiotics," Antimicrobial Agents and Chemotherapy 33:19–26 (Jan. 1989).
Hastings and Ellis, "Detection of Antibodies Induced in Rainbow Trout by Different *Aeromonas salmonicida* Vaccine Preparations," J. of Aquatic Animal Health 2:135–140 (1990).
Kay et al., "Properties, Organization and Role in Virulence of the Surface Protein Array of *Aeromonas salmonicida*", Pathology in Marine Aquaculture (Pathogolie en Aquaculture Marine) 217–229 (1986).
Lund et al., "Humoral immune response in Atlantic salmon, Salmo salar L., to cellular and extracellular antigens of *Aeromonas salmonicida*," J. of Fish Diseases 14:443–452 (1991).
Marquis and Lallier, "Efficacy studies of passive immunization against *Aeromonas salmonicida* infection in brook trout, *Salvelinus fontinalis* (Mitchill)," J. of Fish Diseases 12:233–240 (1989).
McCarthy et al., "*Aeromonas salmonicida*: determination of an antigen associated with protective immunity and evaluation of an experimental bacterin," J. of Fish Diseases 6:155–174 (1983).
McCarthy and Roberts, "Furunculosis of fish—the present state of our knowledge," Advances in Aquatic Microbiology, vol. 2 (M. R. Droop & H. W. Jannasch, Eds.), Academic Press, London (1980).
Norqvist et al., "Protection of Rainbow Trout against Vibriosis and Furunculosis by the use of Attenuated Strains of *Vibrio anguillarum*," Applied and Environmental Microbiology 55:1400–1405 (Jun. 1989).
Olivier et al., "Immunogenicity of vaccines from a virulent and an arivulent strain of *Aeromonas salmonicida*," J. of Fish Diseases 8:43–55 (1985).
Singer et al., "Use of a restriction–defective variant for the construction of stable attenuated strains of the marine fish pathogen *Vibrio anguillarum*", J. of Microbiological Methods 13:49–60 (1991).
Thornton et al., "Surface–disoriented, attenuated mutants of *Aeromonas salmonicida* as furunculosis live vaccines," Microbial Pathogenesis 11:85–99 (Oct. 1991).
Trust et al., "Properties of A Protein, a Virulence Factor on the Surface of *Aeromonas salmonicida*," Developmental and Comparative Immunology Supplement 2 pp. 175–180 (1982).
Trust et al., "Virulence Properties of *Aeromonas salmonicida*," J. World Maricul. Soc. 14:193–200 (1983).
Vaughan et al., "Aromatic–Dependent Mutants of *Aeromonas salmonicida*," Res. Microbiol. 141:941–943 (1990).
Wood et al., "Multiple Low–Level Antibiotic Resistance in *Aeromonas salmonicida*," Antimicrobial Agents and Chemotherapy 29:992–996 (Jun. 1986).
Ishiguro et al., "Loss of Virulence During Culture of *Aeromonas salmonicida* at High Temperature," Journal of Bacteriology, 148:333–340 (Oct. 1981).
Ishiguro et al., "Congo Red Agar, a Differential Medium for *Aeromonas salmonicida*, Detects the Presence of the Cell Surface Protein Array Involved in Virulence," Journal of Bacteriology, 164:1233–1237 (Dec. 1985).

Primary Examiner—Hazel F. Sidberry
Assistant Examiner—Julie Krsek-Staples
Attorney, Agent, or Firm—Klarquist Sparkman Campbell Leigh & Whinston

[57] ABSTRACT

Novel attenuated strains of *Aeromonas salmonicida* are disclosed that are effective as live effective vaccines against furunculosis in fish. These vaccines may be administered by the immersion of fish in a solution of the vaccine. Methods of producing these strains and other strains having the identifying characteristics of these strains are also disclosed.

**34 Claims, 6

ATTENUATED STRAINS OF *AEROMONAS SALMONICIDA* USEFUL AS FISH VACCINES

FIELD OF THE INVENTION

This invention concerns attenuated microorganisms useful as live vaccines against furunculosis disease in fish.

BACKGROUND OF THE INVENTION

*Aeromonas salmonicida* is a non-motile, facultatively anaerobic, Gram-negative rod-shaped bacterium of the Vibrionaceae family. It is the etiological agent of salmonid furunculosis, a disease capable of causing serious losses in both cultured and wild stocks of salmonids such as the Pacific salmon (*Oncarhynchus sp.*), rainbow trout (*O. mykiss*), and the Atlantic salmon (*Salmo salar*).

The use of antibiotics to treat furunculosis disease in fish has encountered some significant problems, primarily the development of antibiotic resistance in the causative microorganisms. Extensive research has therefore been performed in recent years to develop vaccines to prevent this disease. Vaccines previously developed for the prevention of furunculosis have included killed bacteria (bacterins) administered either orally, by injection, or by immersion or spraying (Klontz and Anderson, 1970; Paterson and Fryer, 1974; Michel, 1979; McCarthy et al., 1983; Johnson and Amend, 1984; Olivier et al., 1985; Tatner, 1987). So far, injection is the only route of administration which has provided reasonable immunity against this disease in fish. Injectable vaccines are not as practical or desirable as immersion vaccines for vaccinating large salmonid populations because injections are time-consuming, expensive and cause physiological stress in the fish. In spite of a strong commercial demand and extensive research, an effective vaccine for furunculosis that does not require administration by injection, has eluded researchers since the first oral vaccine trials of Duff (Duff, 1942).

Recently, the production of live, attenuated bacterial vaccines has received a great deal of attention. Live vaccines generally produce a more effective immunity compared to vaccines based on killed pathogens or bacterial components. Furthermore, live vaccines may require a smaller dose than killed pathogens or single bacterial component vaccines and may be less expensive to produce. The production of bacterial component vaccines requires potentially complex purification steps while the production of killed pathogen vaccines requires very careful control and assessment of the product to ensure that no live pathogens remain.

Some live, attenuated vaccines have been developed, primarily for the prevention of enteric salmonellosis (Hoiseth and Stocker, 1981; Sigwart et al., 1989). These vaccines have employed a variety of compromising mutations, most of which would be difficult to reproduce in *A. salmonicida* which is nutritionally fastidious and physiologically unexplored. In some instances, spontaneous antibiotic resistant mutants of bacterial pathogens have been demonstrated to be both avirulent and immunogenic (Brubaker and Surgella, 1962; Cipriano and Starliper, 1982; Bolin et al., 1985; Norqvist et al., 1989) and may offer some potential as vaccines.

However, a major concern with the use of these spontaneous attenuated mutants as vaccines is the frequency of reversion of such mutants to the virulent form. A single point mutation may revert with a frequency as high as $10^{-7}$, resulting in the conversion of the attenuated strain back to the virulent pathogen. Because of this high reversion frequency, such mutants could not safely be released into the environment as a live vaccine and would therefore be unsuitable for use in large scale fish farming.

Recently, genetically engineered attenuated mutants of *A. salmonicida* (Vaughan et al., 1990) and another fish pathogen, *Vibrio anguillarum*, have been produced (Singer et al., 1991; Norqvist et al., 1989). Genetically engineered attenuated strains have a number of potential drawbacks as vaccines, such as the inclusion of antibiotic resistance markers in the engineered organisms which could be spread to other pathogens. The potential for reversion to virulent forms also needs—to be considered, especially where the avirulence is caused by (readily reversible) transposon mutagenesis. Thus, extensive research will be required to ensure the safety and predictability of a genetically engineered attenuated form of a pathogenic organism before it can be released into the environment.

In attempts to elucidate aspects of *A. salmonicida* which might provide insight into the development of effective vaccines, a number of studies have addressed the virulence properties of the organism. Among other aspects of the organism's physiology and metabolism that may influence virulence, the A-layer has received considerable attention (Trust et al., 1982; Trust et al., 1983; Ellis et al., 1988; Kay et al., 1986; McCarthy et al., 1983; Olivier et al., 1985). *Virulent A. salmonicida* strains possess a distinct surface layer (the A-layer) external to the outer membrane. This A-layer is organized as a tetragonal array and is primarily composed of a 50,000 $M_r$ protein termed the A-protein, associated with lipopolysaccharide (LPS). The layer has been shown to completely envelop *A. salmonicida* cells, and to physically protect underlying outer membrane components from bacteriophage, complement and proteolytic digestion. LPS has been shown to be essential in maintenance of A-layer integrity since LPS deficient ($LPS^-$) mutants are invariably A-layer deficient ($A^-$) as well.

Studies with a variety of isogenic strains ($A^+LPS^+$, $ALPS^+$, $A^-LPS^-$) indicate that the A-protein is largely responsible for the hydrophobic nature of the cell surface of virulent strains. A-layer deficient strains are rapidly cleared from fish and, when present, the A-layer enhances adsorption of bacteria to macrophages and appears to confer resistance to the cellulolytic activity of these phagocytes.

It has been suggested that the A-layer is a primary virulence factor in *A. salmonicida*, aiding in survival of the pathogen and enhancing its spread (Trust et al., 1982; Trust et al., 1983; Kay et al., 1986). Trust et al. (1982) have stated that in order to resist infection by *A. salmonicida*, "fish immunelogical defense mechanisms likely need to recognize and effectively respond to this A-protein." The A-protein has therefore been considered an obvious candidate for inclusion in vaccines.

Olivier et al. (1985) compared the immunogenicity of virulent and avirulent *A. salmonicida* strains by injection into fish and rabbits. The results of this study showed that avirulent strains were inferior immunegens and it was suggested that the superior immunogenic properties of the virulent strains were conferred by the A-layer which was believed to be absent from the avirulent strains. McCarthy et al. (1983) demonstrated passive immunity to *A. salmonicida* in fish. This was achieved by raising antisera in rabbits against strains of *A. salmonicida*, including an $A^-$ variant. Fish were injected with these antisera and the protection afforded by each antiserum was assessed by challenge with virulent *A. salmonicida*. Only antisera raised against $A^+$ strains of the organism were found to confer passive immunity, suggesting that this immunity was due to anti-protein-A antibodies. Furthermore, these researchers also tested a number of bacterin vaccines, including an A⁻ variant, by immersion of fish in the bacterin vaccine followed by challenge with virulent *A. salmonicida*. Only bacterins made from A⁺ *A-salmonicida* were effective in protecting the fish, leading the authors to conclude that "[t]he A-protein of *A. salmonicida* is . . . needed to confer protection with bacterins" (McCarthy et al.,1983). Thus the immunogenicity of spontaneous, A-layer deficient, avirulent mutants has generally been found to be insufficient for their use as effective vaccines.

Cipriano and Starliper (1982) described a spontaneous, avirulent mutant that did confer protection against infection when administered by immersion, however the nature of this mutation is unknown and this finding has not been reproduced by others. It is also important to reiterate the dangers of reversion to virulence inherent in such spontaneous mutants.

Despite various attempts to formulate reliable vaccines against *A. salmonicida* infection which can be administered to fish orally or by immersion, suitable vaccines have not been developed to date.

It is an object of this invention to provide an improved live, attenuated vaccine that can reduce the susceptibility of fish to infection by *A. salmonicida*.

It is a further object of this invention to provide an improved live attenuated vaccine for *A. salmonicida* that can be released into the environment without significant potential for reversion of the organism into the virulent progenitor form.

Finally, it is an object of this invention to provide a live attenuated vaccine that may be administered to fish orally or by immersion, yet has efficacy comparable or superior to a vaccine administered by peritoneal injection.

SUMMARY OF THE INVENTION

The foregoing objects have been achieved by the production and isolation of attenuated strains of *A. salmonicida*. These strains are derivatives of the wild-type virulent *A. salmonicida* strain A450 and are capable of inducing protective immunity against infection by virulent *A. salmonicida* in a susceptible fish. Thus, these vaccines are effective in the prevention of furunculosis disease in fish. More specifically, these vaccines are shown to be capable of inducing protective immunity against infection by virulent *Aeromonas salmonicida* in a susceptible fish when administered by immersion of the fish in a solution containing a sufficient amount of the live vaccine for a sufficient period of time to reduce the susceptibility of the fish to infection by virulent *Aeromonas salmonicida*. In particularly preferred embodiments, the fish are immersed in a solution of the vaccine more than once so as to confer particularly effective immunity.

Specifically, the present invention includes the attenuated *A. salmonicida* strains 10S, 10SR, 10SR-3 and A450-3. The present invention also includes biologically pure cultures of each of these strains. In addition to the strains of attenuated *A. salmonicida* named above, the present invention also includes the methods by which these and other immunogenic attenuated strains can be obtained and thereby also encompasses other attenuated *A. salmonicida* strains having the identifying characteristics of the specific strains disclosed in the present invention.

Strains 10SR, 10SR-3 and A450-3 are shown to be effective as live vaccines; strain 10S is an intermediate in the process by which strains 10SR, 10SR-3 and strains having the identifying characteristics of strains 10SR and 10SR-3 are produced and is therefore useful for the production of these strains.

Strain 10S is apparently the first mutant microorganism to be described as totally lacking in membrane cytochromes. Strain 10S and other strains having the identifying characteristics of this strain may be obtained by the process presented in this invention. This process is novel a two step antibiotic-resistance selection process, comprising: (1) selecting a first antibiotic resistant, attenuated strain by growing a virulent progenitor strain of *Aeromonas salmonicida* in the presence of an aminoglycoside antibiotic at a level of 10 µg–100 µg antibiotic per milliliter of culture; (2) selecting a second aminoglycoside antibiotic resistant, attenuated strain lacking in membrane cytochromes by growing the first aminoglycoside antibiotic resistant attenuated strain in the presence of an aminoglycoside antibiotic at a level of 100 µg–2000 µg antibiotic per milliliter of culture. Strain 10S and strains having the identifying characteristics of this strain form a novel starting point for the development of attenuated vaccine strains.

Strain 10SR is an attenuated strain of *A. salmonicida* useful as a live, attenuated vaccine that can be effectively administered to fish by immersion. Strain 10SR is derived from strain 10S by an additional (third) mutation step which comprises growing the slow-growing strain 10S in the absence of the aminoglycoside antibiotic and selecting fast growing revertants.

Thus, strain 10SR is derived from the wild-type virulent *A. salmonicida* strain A450 by a process comprising three mutation steps whereby the characteristics of the progenitor strain are successively changed. Correspondingly, three back-mutation steps would be required to revert strain 10SR to the wild-type virulent *A. salmonicida* strain A450. Such reversion is theoretically shown to occur at the extremely low frequency of $10^{-21}$, and no revertants were observed in experiments designed to detect them, suggesting that the creation of 10SR may have involved an essentially irreversible mutation step. Strain 10SR may therefore be used as a live, attenuated vaccine in the environment (for example, in fish farms) without significant risk of reversion to the wild-type virulent *A. salmonicida* strain A450.

In comparative studies, strain 10SR is shown to be effective as a live vaccine and to be at least as effective when administered by the preferred immersion route as conventional bacterin vaccines are when administered by intraperitoneal injection.

Also provided by the present invention is *A. salmonicida* strain 10SR-3. Strain 10SR-3 lacks the surface A-layer found on strain 10SR and wild-type strains such as strain A450. Strain 10SR-3 is derived from strain 10SR by an additional (fourth) mutation step which comprises growing strain 10SR at a temperature of between 25° C. and 37° C. and selecting strains that lack an A-layer. Strain 10SR-3 is shown to be even more effective than 10SR as a live vaccine that can be administered by immersion of fish. Furthermore, strain 10SR-3 is derived from the wild-type virulent strain A450 by four distinct mutation steps, such that the theoretical reversion frequency of strain 10SR-3 to the virulent progenitor strain is $10^{-28}$, making this strain theoretically even less likely than strain 10SR to revert to the progenitor virulent wild-type strain A450. Two types of mutation process are therefore combined in strain 10SR-3: the three step antibiotic resistance/reversion process producing an attenuated strain (10SR) which is effective as a live vaccine and can be administered by immersion, and the growth at elevated temperature step whereby the A-layer is lost.

The finding that removal of the A-layer not only maintains the immunogenicity of the microorganisms but actually improves the efficacy of the microorganism as a live vaccine is contrary to the conventional teaching in this field and is entirely novel. The present invention also extends this finding by providing other attenuated strains of A. salmonicida which are effective as live vaccines that can be administered by immersion. These strains include strain A450-3, which differs from the progenitor virulent A450 strain only by the absence of the A-layer.

In presenting this novel approach to making vaccine strains, the present invention therefore includes a method by which other strains of A. salmonicida lacking an A-layer and useful as live vaccines can be produced.

The present invention also includes preferred methods by which vaccines comprising these novel, attenuated vaccine strains are made and used.

The foregoing and other features and advantages of the present invention will become more apparent from the following detailed description and accompanying drawings.

DETAILED DESCRIPTION OF THE INVENTION DEFINITIONS

Figure 1:
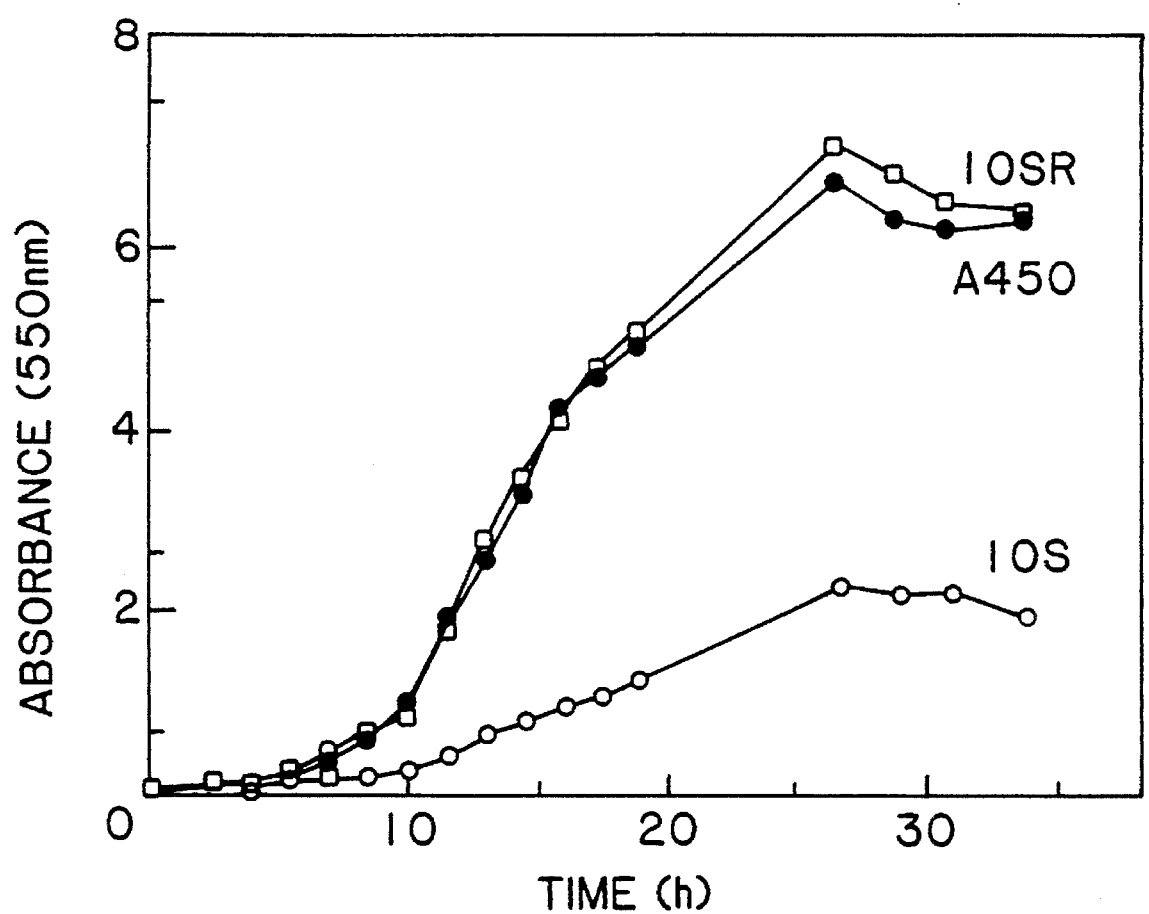
FIG. 1 is a graph showing the growth curves of A. salmonicida strains A450, 10S and 10SR.

A number of terms pertinent to the use of the microorganisms of the present invention as live vaccines are given below:

"Live vaccines" are suspensions of attenuated, live microorganisms, administered for the prevention, amelioration or treatment of an infectious disease.

"Protective immunity" is the condition induced by the administration of a vaccine to a fish wherein the susceptibility of the fish to infection by a particular pathogen is reduced. The extent of protective immunity induced in a fish by a particular vaccine may be measured by determination of the Protective Index.

"Susceptible fish" are those species of fish of which A. salmonicida is a pathogen and in which the live vaccines of the present invention are capable of inducing protective immunity. That is, the microorganism is capable of causing furunculosis in such a fish and the fish is capable of being protected from such disease by vaccination with the vaccines of the present invention. For the purposes of the present invention, susceptible fish species include finfish including, but not limited to salmonid fish including, but not limited to, rainbow trout (Oncorhynchus mykiss), chinook salmon (O. tshawytscha), pacific salmon (Oncorhynchus sp.), sockeye salmon and atlantic salmon (Salmo salar).

"Susceptibility to infection" describes the condition of being a host for a particular pathogen and of suffering injury from the disease caused by that pathogen. The condition of "susceptibility to infection" encompasses a range of susceptibilities. The degree of susceptibility of a particular fish to infection by a particular pathogen may be determined by calculating the $LD_{50}$ value for this pathogen. Fish species less susceptible to infection by a particular pathogen will have a higher $LD_{50}$ for that pathogen than a more susceptible fish species. The capability of a vaccine to reduce the susceptibility of a fish to infection by a pathogen may be determined by calculating the $LD_{50}$ of fish following vaccination; a finding that the $LD_{50}$ value is increased following vaccination is an affirmative indication that susceptibility was reduced. Alternatively, the reduction of susceptibility of a fish to infection by a pathogen may be equated to a particular Protective Index (PI) value; a positive PI value confirms the ability of the vaccine to reduce the susceptibility of the fish to the pathogen. Higher PI values correspond, therefore, to greater reductions in susceptibility.

"$LD_{50}$" values are defined as the concentration of a virulent pathogen, expressed in colony forming units per milliliter (cfu/ml) required to produce 50% mortality in a population of fish. $LD_{50}$ values were calculated based on the method of Reed and Muench (1938). Susceptible fish vaccinated with an effective vaccine will have higher $LD_{50}$ value relative to unvaccinated control fish.

"Protective Index" (or "PI") is a preferred expression of the extent of protection afforded by a particular vaccination regime. The PI value is calculated by dividing the $LD_{50}$ value following vaccination by the $LD_{50}$ obtained for non-vaccinated fish, after challenge with the virulent organism. Thus, by performing control experiments with every vaccination experiment, the PI value allows the results from individual experiments to be compared without consideration of the minor variations in experimental conditions inherent in biological systems. In addition, the PI value gives a quantitative assessment of the level of protective immunity, which is the most important parameter in vaccine trials (Norqvist et al., 1989).

Materials and Methods

Bacterial Strains

A. salmonicida strains A450 and MT26 are wild-type isolates that are virulent in salmonids. The avirulent mutants which comprise a part of the present invention 10S, 10SR, 10SR-3 and A450-3 were derived from A450. These avirulent mutants were deposited with the American Type Culture Collection (ATCC) 12031 Parklawn Drive, Rockville, Md. 20852, U.S.A. on Aug. 28, 1992 and were assigned accession numbers as listed below:

| A. salmonicida Strain 10S | ATCC accession no. 55357 |
| A. salmonicida Strain 10SR | ATCC accession no. 55356 |
| A. salmonicida Strain 10SR-3 | ATCC accession no. 55355 |
| A. salmonicida Strain A450-3 | ATCC accession no. 55354 |

Strain MT26 was used for $LD_{50}$ challenge experiments; it was chosen as a challenge strain because of its exceptionally high virulence.

Media and Culture Conditions

All bacteria were grown in Luria broth (LB) supplemented with modified Davis salts (Lee and Ellis, 1989), (LB-Davis) and 0.2% glucose. Solid media was as above with the addition of 1.5% agar. Streptomycin, where appropriate was routinely added to 500 µg/ml.

Enzyme and Toxin Assays

Protease activity was assayed quantitatively using Hide Powder Azure (Calbiochem) according to the method recommended by the manufacturer, and qualitatively on skim milk agar (0.5% Difco proteose peptone no. 3; 0.2% Difco Yeast extract; 0.85% NaCl; 0.5% skim milk). Siderophore activity was assayed qualitatively by the media method of Schwyn and Neilands as modified by Borghouthi et al. (1989). Haemolytic activity was essayed on human blood agar (HBA-5% whole human blood in Difco Tryptic Soy Agar (TSA)).

Determination of Streptomycin Sensitivity

1:2 serial dilutions of streptomycin in 5 ml Difco Tryptic Soy Broth were made in test tubes. These tubes were then inoculated with $2 \times 10^5$ bacterial cells from overnight cultures. The tubes were incubated at 20° C. for 48 hours. After 48 hours, spectrophotometric readings were taken at 650 nm wavelength (the $A_{650}$ value) and compared to uninoculated control tubes.

An increased $A_{650}$ reading in a particular tube relative to uninoculated control tubes indicates bacterial growth and was taken as an indication of the resistance of that bacterial strain to the level of streptomycin within that tube. A strain that is said to be resistant to a particular concentration of a particular antibiotic is capable of growth in a growth medium containing that particular concentration of that particular antibiotic. It is understood that the growth medium would be capable of supporting the growth of the microorganism in the absence of the antibiotic.

The absence of any increase in absorbance, indicative of no bacterial growth, was taken as an indication of sensitivity of the bacteria to a particular level of streptomycin. Samples were taken from those tubes showing no bacterial growth and plated onto Tryptic Soy Agar (TSA) plates without streptomycin. The plates were incubated for 48 hours at 20° C. and then visually inspected for the presence of bacterial colonies. If no bacterial growth was observed, the concentration of streptomycin in the culture tube from which the sample was taken was assessed to be bacteriocidal. If bacterial growth was observed on the plates, the concentration of streptomycin in the tube from which the culture was taken was assessed to be bacteriostatic. If the growth of a particular microorganism is described as "sensitive to" or "inhibited in" a particular concentration of an antibiotic such as streptomycin, then that antibiotic concentration may either be bacteriostatic or bacteriocidal.

Antibiotic Sensitivity Profiles

Antibiotic sensitivities to a range of antibiotics were determined on solid media using commercially available antibiotic discs. A 50-µl aliquot of a fresh LB grown bacterial culture ($1 \times 10^9$ cells/ml) was spread evenly on LB agar plate and antibiotic discs applied prior to incubation at 20° C. for 2 days. Values were reported as the radius of the zone of inhibition minus the radius of the disc, measured in mm.

Sensitivity to Membrane Antagonists

Sensitivity to membrane antagonists was assayed using sterile filter disks (6 mm) on which 50 µl of saturated solution of the antagonist was dried. Sensitivities were also expressed in the radius of the zone of inhibition minus the radius of the disc, expressed in min.

Electrophoresis

Samples were separated on sodium dodecyl sulfatepolyacrylamide gels (SDS-PAGE) according to the modified method of Laemmli (Ames, 1974). Proteins were visualized with Coomassie Brilliant Blue R250, and lipopolysaccharides (LPS) with the silver stain method of Tsai and Frasch (1982). Western immunoblots were performed essentially as follows: SDS-PAGE proteins were transferred to nitrecellulose paper as described by Towbin et al. (1979). Following blocking with 2% Bovine Serum Albumin (BSA), the blots were incubated with 2000-fold dilutions of polyclonal rabbit sera directed against formalinized A450 whole cells. After extensive washing, these blots were then incubated with 1 µg/ml alkaline phosphatase conjugated goat anti-rabbit antibodies (Caltag), and developed according to the manufacturer's recommendations. All incubations and washes were performed in 1.5 mM NaCl, 5 mM EDTA, 50 mM Tris, pH 7.4 (NET buffer), containing 0.05% NP40 (Sigma Chemical Co.).

Oxygen Utilization Assays

Whole cells, harvested from exponentially growing aerated cultures, were washed in PBS (10 mM phosphate; 0.85% NaCl; pH 7.2) and starved from 1 to 24 h in the same buffer. These suspensions were resuspended to 5 mg wet cells/ml in 3 ml modified Davis salts media and added to the incubation chamber of a Clarke style oxygen electrode (YSI model 53). After monitoring the baseline the carbon source was added to 30 mM and the consumption of $O_2$ monitored.

Cytochrome Scan

Qualitative and quantitative determination of individual cytochrome contents of the *A. salmonicida* strains were preformed in a dual beam spectrophotometer. Low temperature (77 K.) difference spectra (dithionite reduced minus perioxide oxidized) were generated essentially by the method of Bott et al. (1990) with the exception that the oxidation of cytochromes was carried out by addition of $H_2O_2$. Using this method the various cytochromes can be identified.

Cell Fractionation

Cell free culture supernatants were obtained by centrifugation ($10^4 \times g$ at 4° C. for 15 min). Cell fractions for electrophoresis were obtained after rupturing the cells in a French pressure cell (1100 kg/cm$^2$). Whole membranes were obtained by centrifuging lysed cell suspensions at $10^5 \times g$ at 4° C. for 1 hour. Outer membranes were prepared by solubilization of the inner membrane with 0.5% sodium lauryl sarcosinate (Filip et al., 1973). Periplasmic fractions were obtained by the sucrose-EDTA osmotic shock method of Willis et al. (Willis et al., 1974).

Protein Separation

When necessary, culture supernatants were concentrated prior to electrophoresis by ammonium sulphate or trichloro acetic acid (TCA) precipitation. Ammonium sulphate was added to 85% saturation at 0°C with gentle stirring, then left overnight at 4° C. and centrifuged at $1.5 \times 10^4 \times g$ for 30 min. TCA precipitation was accomplished by adding an equal volume of cold 20%TCA to samples on ice, followed by centrifugation and a −20° C. acetone wash. The resulting pellets were resuspended in appropriate volumes of SDS-PAGE sample buffer. Protein concentrations were measured by the modified Lowry method of Markwell et al. (Markwell et al., 1978).

Electron Microscopy

Negative staining of whole cells and the A-layer was carried out by taking direct impressions from bacterial colonies grown on TSA media (taken by touching the surface of a colony with a Formvar coated copper grid). The grids were then immediately floated on unbuffered saturated ammonium molybdate for staining.

Immunogold labelling was performed essentially by the method of DeMay and Moermans (1986). Briefly, bacterial cells were fixed in 4% fresh depolymerized paraformaldehyde and 0.1% glutaraldehyde in 10 mM $Na_2HPO_4$; 0.86% NaCl; pH 7.4 (PBS), at room temperature for not less than 2 hours. The fixed cells were pelleted and embedded in 0.3% agarose prior to dehydration and final embedding in LR White resin (London Resin Co. Ltd., Surrey, England). Thin sections mounted on nickel grids, were labelled in situ using polyclonal rabbit IgG directed against A-protein and 10 nM protein A-gold probe (Janssen Biotech, NV, Olen, Belgium).

Specimens were examined in a Philips EM 300 transmission electron microscope (Philips Electronic Instruments Inc., Mahwah, N.J.) at an accelerating voltage of 60 kV.

Virulence and Protection

All fish were maintained at 13° C. (±1° C.) in a continuous flow of dechlorinated city water before and during experiments.

Virulence of individual bacterial strains was assayed by intraperitoneal (i.p.) injection of $1 \times 10^8$ colony forming units (cfu) of the test organism into 5–10 g juvenile chinook salmon (*O. tshawytscha*). Virulence was expressed as % mortality occurring within 18 days of injection. Tissue persistence was assayed by the incubation of 0.1 g tissue samples, from fish killed in virulence assays, in LB Davis medium for 72 hours at 20° C. followed by examination of plated samples for typical pigment producing colonies on TSA with antibiotics added where appropriate.

Serum resistance of the bacteria was determined essentially by the method of Munn et al. (1982) using fresh human sera. Control samples were heat inactivated by heating serum to 55° C. for 15 minutes.

Protection assays were performed according to the method of Newman and Majnarich (1985). For injection vaccinations, fish were injected i.p. with $10^7$ cells of the vaccine strain (or bacterin equivalent), in 0.85% saline. Immersion vaccinations were carried out by immersing fish in a suspension of the vaccine strain containing $5 \times 10^8$ cfu/ml (or bacterin equivalent) for 30 minutes unless otherwise stated. The number of times of immersion were varied in individual experiments.

The vaccinated and control fish were challenged by immersion exposure to the virulent *A. salmonicida* strain MT26. Several challenge dosages (in the range of $10^6$–$10^9$ cfu/ml of MT26) were utilized. For each challenge dosage, groups of 10 fish were immersed in an appropriate concentration of MT26 for 30 minutes. Challenges were carried out 14 days after vaccination, and these challenge experiments were terminated when death attributable to *A. salmonicida* ceased (not less than 18 days). $LD_{50}$ values were calculated based on the method of Reed and Muench (1938). The Protective Index (PI) of a particular vaccination regime was calculated by dividing the $LD_{50}$ value following vaccination by the $LD_{50}$ obtained for nonvaccinated fish, after challenge with the virulent MT26 strain.

For these protection studies, the heterologous *A. salmonicida* strain MT26 was always used as a virulent challenge strain, and 5–10 g rainbow trout (*O. mykiss*) were used as the animal model.

Isolation of Strains

The strains of the present invention were all derived from the progenitor *A. salmonicida* strain A450.

Isolation of *A. salmonicida* strain 10S 10S is an aminoglycoside antibiotic resistant, attenuated strain of *A. salmonicida*. A strain that is said to be resistant to a particular concentration of a particular antibiotic is capable of growth in a growth medium containing that particular concentration of that particular antibiotic. Strain 10S is resistant to 1 mg/ml of streptomycin; that is, it is capable of growth in a growth medium ordinarily capable of supporting the growth of the strain (for example, LB-Davis+ 0.2% glucose) when streptomycin is added to the medium to a concentration of 1mg/ml. Strain 10S was derived from the progenitor wild-type, virulent *Aeromonas salmonicida* strain A450 by a two-step selection process as described below.

For the first selection step, *A. salmonicida* strain A450 was grown in LB Davis+0.2% glucose to a culture density of $OD_{600}=1$. Streptomycin (a typical aminoglycoside antibiotic) was then added to this broth culture to a final concentration of 100 μg/ml. This culture was grown for 24 hours at 20° C. Cells resistant to 100 μg/ml streptomycin were found to arise at a frequency of approximately $1 \times 10^{-7}$. The culture was then plated on TSA agar containing streptomycin at a concentration of 500 μg/ml for the second step of the selection process. The inoculated TSA/streptomycin plates were then incubated at 20° C. for 72 hours. After incubation resistant colonies (arising at a frequency of approximately $1 \times 10^{-7}$) were restreaked on the same medium for purity.

*A. salmonicida* strain 10S is typical of the 500 mg/ml streptomycin resistant mutants that were isolated; strain 10S is resistant to at least 1 mg/ml streptomycin and, as described below, strain 10S is phenotypically very different from the progenitor A450 strain. In particular, 10S is apparently completely devoid of membrane cytochromes and grows more slowly and to a lower cell density compared to the A450 progenitor strain.

Having set forth the process by which strain 10S was derived, one skilled in the art will recognize that the process set forth is illustrative only of the process and that variations on this process will also be effective in isolating strain 10S. For example, different levels of streptomycin may be used at the two selection stages. In preferred embodiments, the streptomycin concentration used in the first selection step is within the range of 10 μg–100 μg per milliliter of culture, and is within the range of 100 μg–2000 μg per milliliter of culture in the second selection step. In the most preferred embodiment, the concentration of streptomycin is 100 μg per milliliter of culture and 500 μg per milliliter of culture in the first and second selection steps respectively.

Other possible variations will also be apparent to one skilled in the art. These variations include the type of growth medium used and the aminoglycoside antibiotic selected. Other suitable aminoglycoside antibiotics include, but are not limited to, kanamycin, gentamicin and netilmicin. The resistance of strain 10S to other aminoglycoside antibiotics is illustrated in Table 1 below. These and other variations that differ from the process set forth in arrangement and detail without departing from the principles of the two step selection process are enabled by the present invention and fall within the scope of the invention.

It will also be apparent to one skilled in the art that the process described may be used for isolating other strains having the identifying characteristics of strain 10S and is not limited to isolating strain 10S per se. In providing this process, the present invention also provides strain 10S and strains having the identifying characteristics of strain 10S.

Furthermore, it will be apparent to one skilled in the art that the choice of starting strain is not limited to *Aeromonas salmonicida* strain A450. Any typical wild-type, virulent strain of *A. salmonicida* may be used as the starting strain. Such strains may be obtained from the American Type Culture Collection or other collections including the National Collection of Marine Bacteria, Torry Research Station, Aberdeen, Scotland (NCMB). Alternatively, suitable strains may be readily be isolated de novo from fish inflicted with furunculosis (Norqvist et al., 1989; Wood et al., 1986).

Isolation of *A. salmonicida* Strain 10SR

When strain 10S was grown on TSA without streptomycin, fast growing streptomycin sensitive (Str$^s$) revertants arose at a frequency of $1\times10^{-7}$ above the slow growing 10S background. Typically, the fast growing revertants formed isolated visible colonies on the TSA agar after 60–72 hours incubation at 20° C. The slow growing strain 10S typically requires 120 hours of incubation under the same conditions to form visible colonies. In preferred embodiments of the present invention, those isolated colonies of revertant microorganisms which grow to visible size in 72 hours or less are selected. It will be apparent to one skilled in the art that other fast growing revertants may be obtained by this methodology and also that minor variations on the methodology presented (for example, in the composition of the growth medium) may be made without substantially affecting the efficacy of the technique.

One of the fast-growing revertants, named *A. salmonicida* strain 10SR, was selected for further study and purified by repeated single colony isolation. Repeated attempts to revert 10SR to either a 10S or A450 phenotype were unsuccessful suggesting that a separate non-reverting mutation, perhaps due to a deletion or genomic rearrangement, led to 10SR. As described below, strain 10SR has regained many of the membrane cytochrome functions that were absent in strain 10S (a membrane cytochrome negative strain). Thus, strain 10SR is a revertant of a membrane cytochrome negative *Aeromonas salmonicida*.

It will be appreciated by one skilled in the art that the methodology described herein will facilitate the isolation of other strains having the characteristics of strain 10SR and is not limited to strain 10SR per se.

Isolation of *A. salmonicida* Strains 10SR-3 and A450-3: A-layer Deficient Strains of *A. salmonicida*

Growth of *A. salmonicida* in liquid culture at higher than optimal temperature (i.e., at or about 25° C.) results in selection of spontaneous avirulent derivatives in the bacterial population of the inoculant. These derivatives have been shown to lack the A-layer found in the virulent progenitor strains (Trust et al., 1982). As described above, conventional teachings have suggested that the presence of the A-layer on *A. salmonicida* strains is required if the organism is to be effective as a vaccine (Olivier et al., 1985).

For the purposes of this invention, both the progenitor *A. salmonicida* A450 strain and the *A. salmonicida* 10SR attenuated strain were grown at elevated temperatures (30° C.) in order to obtain spontaneous A-layer deficient mutants. Such mutants were detected by the inability of mutant colonies to take up congo red dye from congo red agar. Specifically, the parental strains were grown to saturation overnight in TSB at 20° C. Aliquots of these cultures were then plated on TSA+30 μg/ml congo red and incubated at 30° C. for 24–48 hours. White colonies arising on these plates were picked, restreaked and confirmed as A-layer deficient variants by SDS/PAGE. Alternatively, these mutant colonies may be detected by the inability to take up Coommassie blue dye. A-layer deficient strains of *A. salmonicida* A450 and *A. salmonicida* 10SR are typified by strains *A. salmonicida* A450-3 and *A. salmonicida* 10SR-3 respectively. While 30° C. was used to obtain the A-layer deficient strains in the present invention, it will be appreciated by one skilled in the art that a range of temperatures may be used to achieve the same result. In other embodiments of the present invention, the step of obtaining A-layer deficient strains may be performed by growing the progenitor strain at a temperature of between 25° C. and 37° C. In a preferred embodiment of the present invention, the step of obtaining A-layer deficient strains is performed by growing the progenitor strain at a temperature of 30° C. The A-layer deficient status of these strains is also confirmed by electron microscopy using immunogold labelling (anti-A-protein IgG as a primary antibody and protein A-colloidal gold conjugate as a secondary label) as described above. Additionally, SDS-PAGE may be used to confirm the deficiency of A-protein in these strains. Any of these numerous techniques may be used as screening techniques for A-layer deficient strains.

Growth Rates of *A. Salmonicida* Strains A450, 10S and 10SR

FIG. 1 shows the growth curve of strain A450 in comparison to the mutant strains 10S and 10SR. All cultures were 100 ml of LB medium in 500 ml flasks and were grown at 20° C. with shaking at 250 revolutions per minute (rpm). One absorbance unit is equivalent to 0.35 mg dry weight of cells/ml. Strain 10S clearly grows at a much reduced rate and to a lower cell density compared to A450. Strain 10SR shows a growth pattern that is similar to A450.

Phenotypic Properties of 10S and 10SR

When the mutant 10S and its apparent revertant 10SR were screened for the classical virulence phenotypes associated with virulent *A. salmonicida*, (Trust, 1986) it was found that both strains resembled the virulent parental strain A450 with respect to these markers. Thus these strains were agglutinated by specific antiserum to the A-protein of the A-layer (Kay et al., 1981), and to lipopolysaccharide (LPS) (Chart et al., 1984), and were positive for extracellular hemolysin and proteases (Ellis et al., 1981), as well as siderophores (Chart and Trust, 1983). Therefore, the ability of these mutants to synthesize the principal surface antigens was qualitatively unimpaired, and the secretion of the usual extracellular proteins was quantitatively unimpaired.

Antibiotic sensitivity profiles (Table 1) indicated that 10S harbours a mutation that confers general low level resistance to aminoglycoside antibiotics, and that 10SR had, at least with respect to this phenotype, reverted to wild-type sensitivity. It is interesting to note that the 10S and 10SR have wild-type sensitivities to both penicillin and tetracycline.

TABLE 1

Antibiotic sensitivities of A450, 10S and 10SR

| Antibiotic[b] | Sensitivity (mm)[a] | | |
|---|---|---|---|
| | A450 | 10S | 10SR |
| Sm | 4 | 0 | 4 |
| Nm | 5 | 0 | 4.5 |
| Tm | 6 | 1 | 6 |
| Vm | 0 | 0 | 0 |
| Km | 6 | 1.5 | 0 |
| Gm | 0.5 | 0.5 | 5 |
| Am | 1 | 0 | 1 |
| Pen | 15 | 16 | 16 |
| Tc | 9 | 9.6 | 9 |

[a]Values represent the zones of growth inhibitions (radius of zone minus disk radius).
[b]Sm: streptomycin; Nm: neomycin; Tm: tobramycin; Vm: Vancomycin; Km: kanamycin; Gm: gentamycin; Am: aureomycin; Pen: penicillin G; Tc: tetracycline.

Cell Composition of A450, 10S and 10SR

Figure 2:
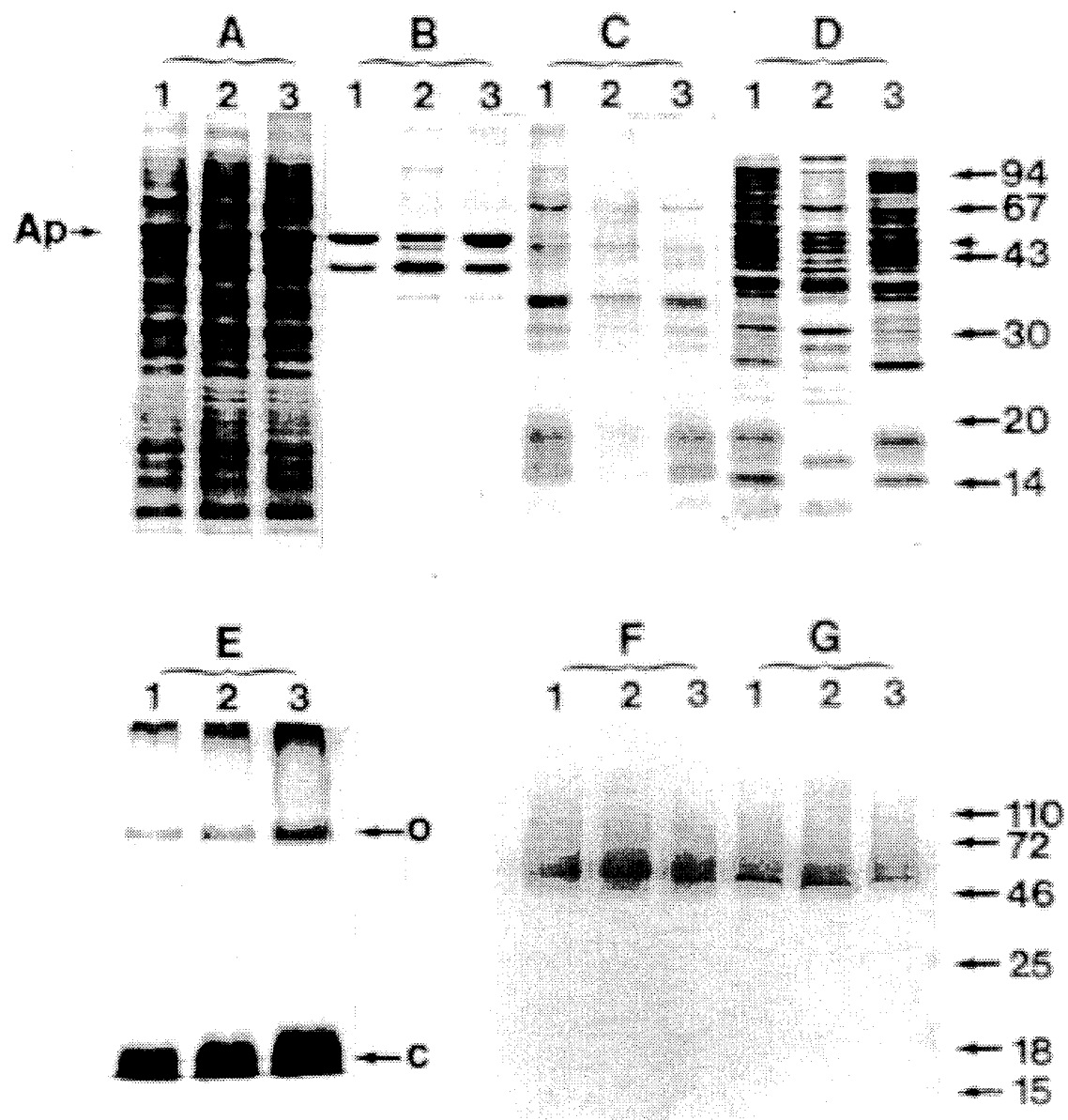
FIG. 2 shows SDS-PAGE analyses of cellular fractions from A. salmonicida strains A450, 10S and 10SR.

To obtain a quantitative assessment of the cell surface composition, both mutant and A450 cells were fractionated into inner membrane, outer membrane, periplasm, and whole cell lysates. The fractions were analyzed by SDS-PAGE combined with protein, silver, and immunechemical staining. FIG. 2 shows sodium dodecyl sulfate-polyacrylamide gel electrophoresis (SCS-PAGE) analyses of cellular fractions from: A450 (lane 1), 10S (lane 2) and 10SR (lane 3). A-D represent Coomassie Blue stained samples of whole cells, outer membrane, inner membrane and periplasm respectively; Ap indicates A-protein. E represents silver stained lipopolysaccharides from the three strains. F and G represent immunoblots of whole cell lysates and outer membranes respectively. The primary antibody was rabbit immune serum raised against formalin fixed whole A450 cells. The secondary antibody was goat anti-rabbit IgG conjugated to alkaline phosphatase. $M_r$ standards are shown in kDa.

Whole cell lysates (FIG. 2A), while naturally complex due to the large number of proteins represented, were similar in most aspects, although small changes would not easily be seen. The outer membrane fractions (FIG. 2B) were not strikingly different since all these strains contained the two principal proteins of this fraction, A-protein (Kay et al., 1984), the main component of the 2D crystalline array (Dooley et al. 1989), and the lower band representing the major outer membrane porin of this strain (Darveau et al., 1983). The ratio of these proteins appeared to be reversed in 10S, but returned to normal in 10SR. The minor protein bands appearing in the outer membrane, particularly with 10S, were unidentified but were virtually absent once more in strain 10SR. The inner membrane fraction (FIG. 2C), indicated that several proteins were either absent—especially those of lower $M_r$—from strain 10S or were grossly under-represented, a pattern which was partially corrected in strain 10SR. However, the periplasmic fraction (FIG. 2D) showed the greatest and clearest difference in protein composition, especially for strain 10S.

The revertant strain 10SR displayed a periplasmic protein profile with distinct minor differences from the wild-type, indicating that a complete reversion to wild-type had not occurred. All three strains still produced their normal complement of liposaccharides (FIG. 2E), comprising the core region lipo-oligosaccharide (lower band) and the O antigen-containing complete LPS, although strain 10SR appeared to produce slightly more LPS than the other strains. In addition, Western blots of whole cell lysates (FIG. 2F) as well as the isolated outer membrane fraction (FIG. 2G), using antisera raised against whole cells of the parent strain, indicated that all three strains were qualitatively and quantitatively immunogenically similar. Importantly, these three strains were strikingly similar with respect to the major cell surface components and immunogens.

Electron Microscopy

Figure 3:
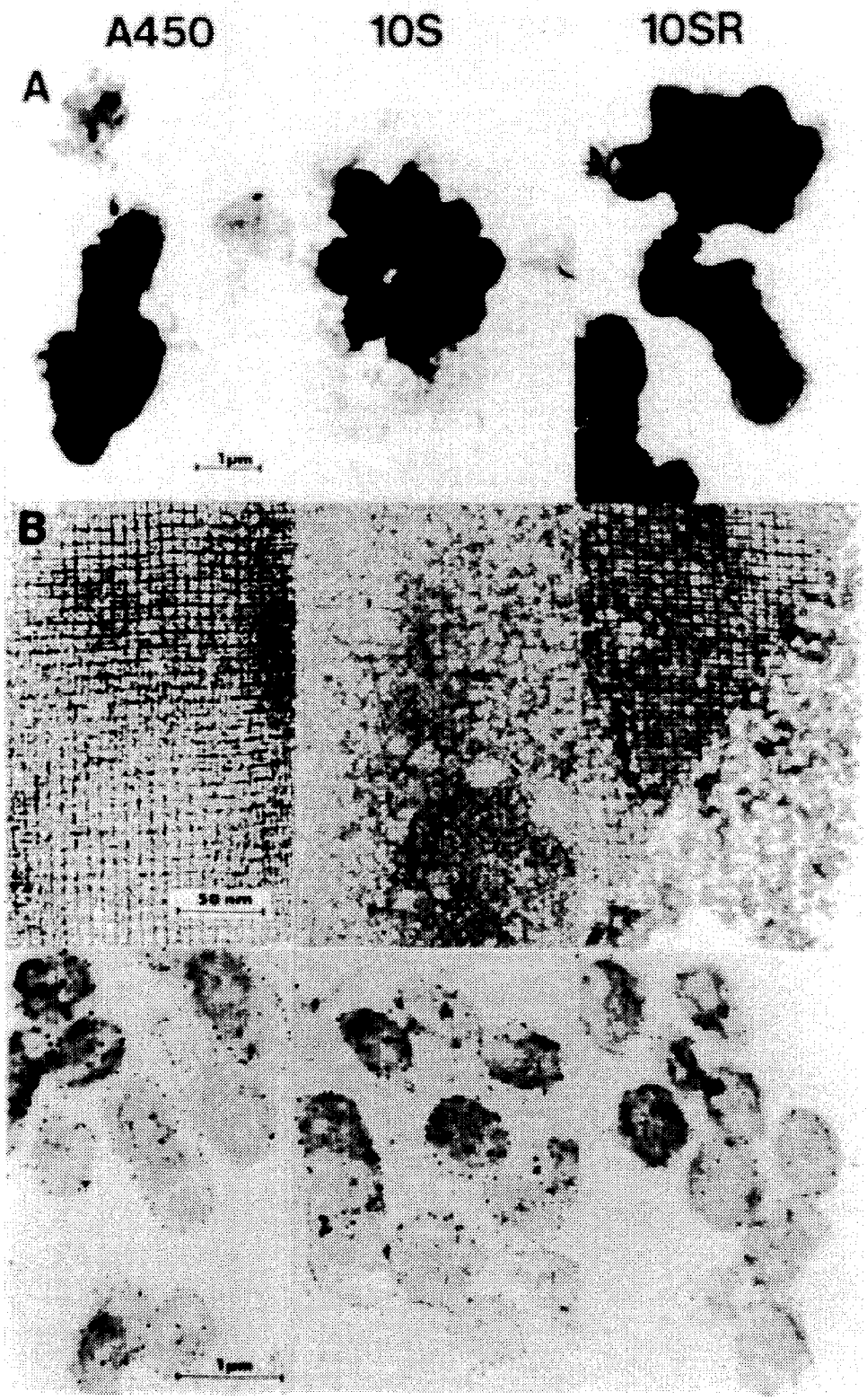
FIG. 3 is a series of electromicrographs of negatively stained whole cells (A), A-layer (B), and immunogold-labeled thin sections (C) of A. salmonicida strains A450, 10S and 10SR.

FIG. 3 shows electron micrographs of negatively stained whole cells (A), A-layer (B), and immunogold labelled thin sections (C) of the strains A450, 10S and 10SR. In (C), the primary antibody was affinity-purified anti-A-protein IgG. The secondary label was protein A-colloidal gold conjugate. The scales for A, B and C are indicated by the bar in the left column. Panel A depicts the cell morphology of the mutants in comparison to the wild-type. Both 10S and 10SR cells are slightly smaller and are, in general, coccoid in form. Panel B represents a negative stain of the A-layer of these organisms. The wild-type A-layer shows the typical 2D tetragonal array; the A-layer from 10SR is seen in some areas to be very similar to the wild-type array (upper split frame), but, in preparations from 10SR colonies older than 3 days, the array was commonly without regular pattern perhaps due to a high degree of stacking of this layer (lower split frame). Panel C represents thin sections of cells treated with anti-A protein immunoglobulin and protein A-colloidal gold conjugate. In the parent strain the colloidal gold label is fairly uniformly distributed at the cell periphery, but becomes unevenly distributed in 10S and even more so in 10SR. These results demonstrate that in all cases the layer is present and peripheral to the outer membrane, but that it adopts different arrangements and disposition in each of the three strains.

Cell Envelope Integrity

Figure 4:
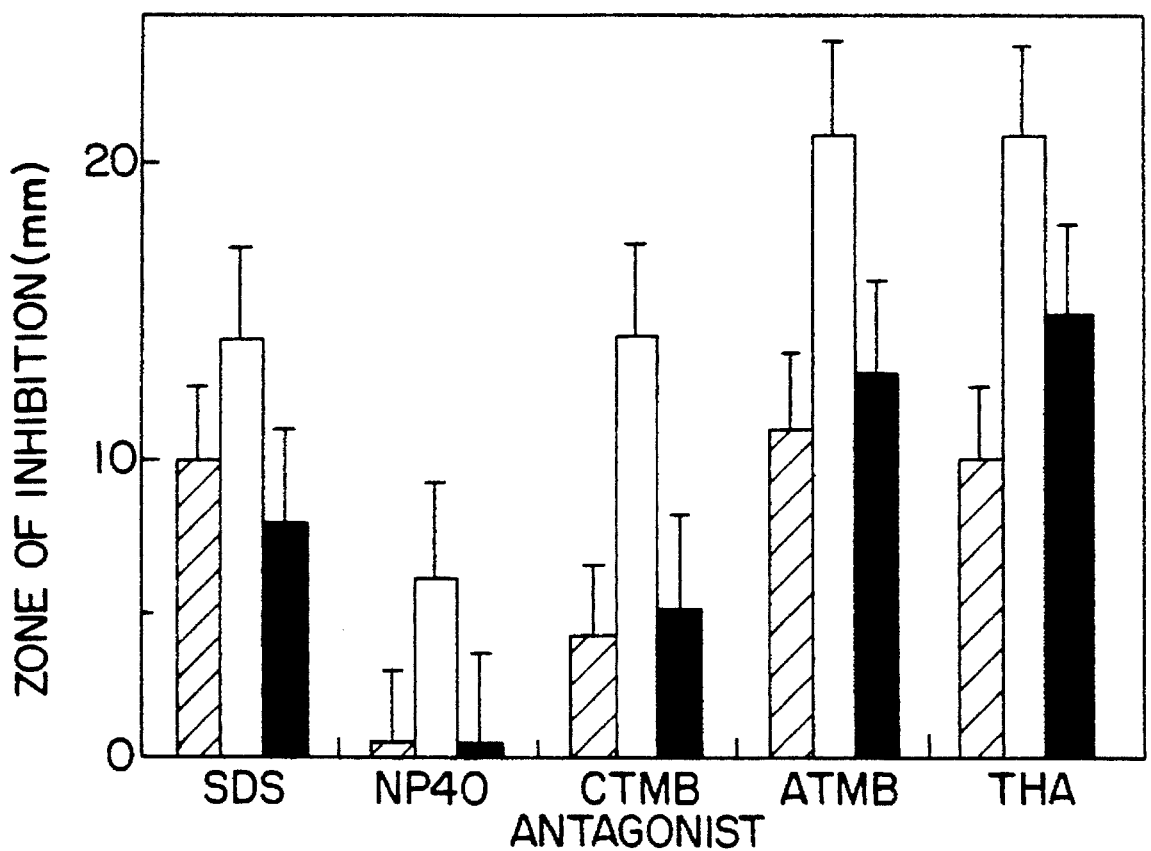
FIG. 4 is a bar graph showing the sensitivity of A. salmonicida strains A450 (hatched columns), 10S (open columns) and 10SR (filled columns) to membrane antagonists.

FIG. 4 shows the sensitivity of strains A450 (hatched columns), 10S (open columns) and 10SR (filled columns) to membrane antagonists. The membrane antagonists used were: sodium dodecyl sulfate (SDS), nonidet P40 (NP40), cetyltrimethyl ammonium bromide (CTMB), alkyltrimethyl ammonium bromide (ATMB), and trihexylamine (THA). Strain 10S was unusually sensitive to non-ionic (NP40), anionic (SDS), and cationic detergents (CTMB, ATMB and THA). Although altered, 10SR was more similar to the wild-type in its sensitivity pattern, being insensitive to non-ionic detergents, less sensitive to the anionic detergent, but slightly more sensitive to the cationic detergents. These studies suggested that changes had occurred in the integrity of the mutants cell surface and/or membranes; the mutant 10S became more sensitive and the apparent revertant 10SR partially regained the properties of the wild-type strain A450.

Oxidative Capacity of Strains A450, 10S and 10SR

The observed reduction in growth rate and yield of 10S, led to the hypothesis that a major disfunction in cellular metabolism and/or energy metabolism had occurred. Capability of the strain to oxidize a particular substrate is performed as described in the materials and methods section above. The method of using an electrode to measure oxygen consumption as an indicator of oxidative metabolism may be used to determine whether a particular strain is capable or incapable of oxidizing a particular substrate. Any consumption of oxygen under the test conditions is indicative that a particular strain is capable, to some degree, of oxidizing the carbon source present. Lack of oxygen consumption indicates that a particular strain is incapable of oxidizing the carbon source present. One skilled in the art will appreciate that the specific methodology presented is illustrative only of the general principle and that variations on the given methodology may be used.

Using a Clarke electrode to monitor oxygen consumption as an indicator of oxidative metabolism it was shown that both 10S and 10SR differed from A450 in their ability to oxidize various carbon sources (Table 2). Strain 10S was incapable of oxidizing any of the carbon sources tested, as evidenced by the lack of oxygen consumption when this strain was supplied with the carbon sources. Strain 10SR regained the ability to oxidize some carbon sources, while only partially regaining the ability to oxidize others. Strain 10SR was capable of oxidizing galactose, lactate, mannose, maltose and peptone but was incapable of oxidizing glucose or xylose. Once more it would appear that 10SR is a partial or pseudorevertant of 10S.

TABLE 2

Oxidation of selected carbon sources by A450, 10S and 10SR

| Carbon source[b] | $O_2$ consumption[a] | | |
|---|---|---|---|
| | A450 | 10S | 10SR |
| Galactose | 1.91 | 0 | 1.55 |
| Glucose | 4.14 | 0 | 0 |
| Lactate | 1.40 | 0 | 1.27 |
| Mannose | 2.16 | 0 | 2.15 |
| Maltose | 1.80 | 0 | 1.20 |
| Xylose | 1.15 | 0 | 0 |
| Peptone[c] | 1.24 | 0 | 1.38 |

[a]Carbon sources were used at a final concentration of 30 mm.
[b]$O_2$ consumption is expressed as ml $O_2$ consumed /hr/mg of wet cells present in the assay.
[c]The peptone used was bactopeptone at 0.1% final concentration.

Determination of Membrane Cytochromes

Figure 5:
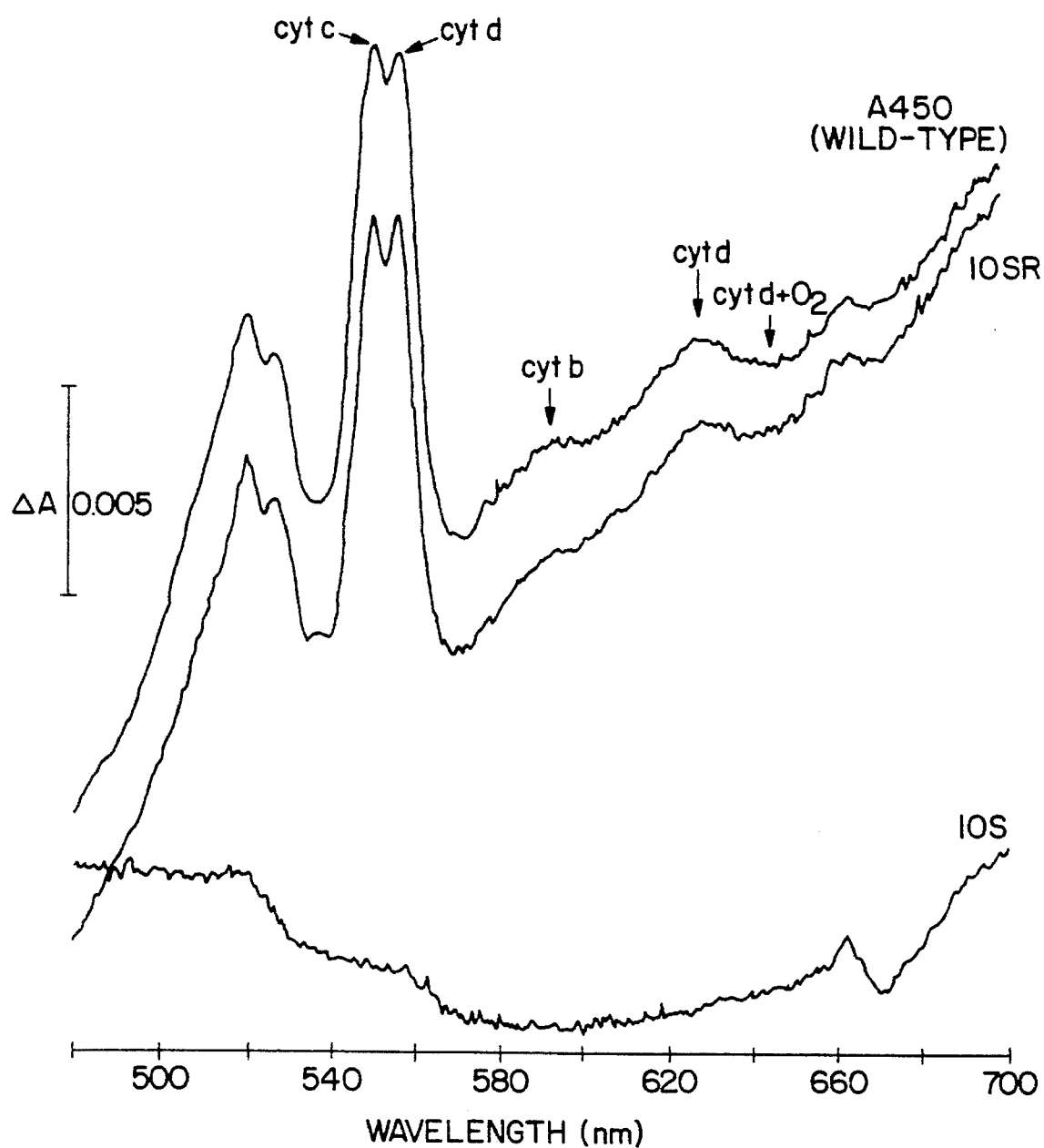
FIG. 5 is a spectrograph showing low temperature difference spectra used for the determination of membrane cytochromes in mutant A. salmonicida strains.

Low temperature difference spectra (dithianiteo reduced—peroxide oxidized) were generated for A450, 10S and 10SR in order to assess the presence of membrane cytochromes. The results of the cytochrome scan are shown graphically in FIG. 5. The cytochrome scan demonstrated that while A450 and 10SR have a normal array of cytochromes, 10S is completely lacking in membrane cytochromes. This absence of cytochromes in strain 10S is referred to herein as a membrane cytochrome negative condition in a membrane cytochrome negative organism.

Virulence of A450, 10S and 10SR

In order to test the virulence of the mutants of A450, 5–10 g juvenile chinook salmon (*O. tshawytscha*) were injected intraperitoneally (i.p.) with an excessive dose ($1 \times 10^8$ colony forming units or cfu, which represents $10^6 \times LD_{50}$ of the virulent challenge strain MT26) of live cells of one of each of the three strains A450, 10S and 10SR. The results of these challenges in which strains 10S and 10SR were shown to be completely avirulent are shown in Table 3.

TABLE 3

Comparison of virulence of strains A450, 10S and 10SR

| Strain | No. Injected* | No. dead# | Mortality (%) |
|---|---|---|---|
| A450 | 30 | 30 | 100 |
| 10S | 30 | 0 | 0 |
| 10SR | 30 | 0 | 0 |

*Chinook salmon (5–10 g) were injected intraperitoneally with $1 \times 10^8$ cfu of the respective strain.
These mortalities represent those fish that died within 18 days.

Tissue Persistence

The tissue persistence of 10SR, was examined at various times after a 30-min immersion of 5–10 g chinook salmon in a 0.85% saline bath containing $1 \times 10^8$ cfu/ml of the mutant strain. Specific target tissues were extracted and cultured as described above. The presence of 10SR was assayed by plating cultured tissues. These results were compared to the spread and persistence of strain A450 in fish tissues (Table 4). Strain 10SR spread throughout the examined tissues in an apparently identical pattern to that of A450, but could only be isolated from kidney up to 48 hours post-infection.

TABLE 4

Tissue persistence of A450 and 10SR

| | Time (h) | | | | |
|---|---|---|---|---|---|
| Strain | 1 | 4 | 12 | 24 | 48 |
| | (presence of the organism)[a] | | | | |
| A450 | | | | | |
| Kidney | ++ | ++ | ++ | ++ | ++ |
| Liver | − | − | + | ++ | ++ |
| Spleen | − | ++ | ++ | ++ | ++ |
| 10SR[b] | | | | | |
| Kidney | ++ | ++ | ++ | ++ | ++ |
| Liver | − | − | + | ++ | − |
| Spleen | − | ++ | ++ | ++ | − |

[a]++: present in >50% tested; +: present in <50% tested; −: absent from all tested. The number of fish tested at each time was four.
[b]10SR was not isolated from any tissue after 48 h.

Serum Resistance

Figure 6:
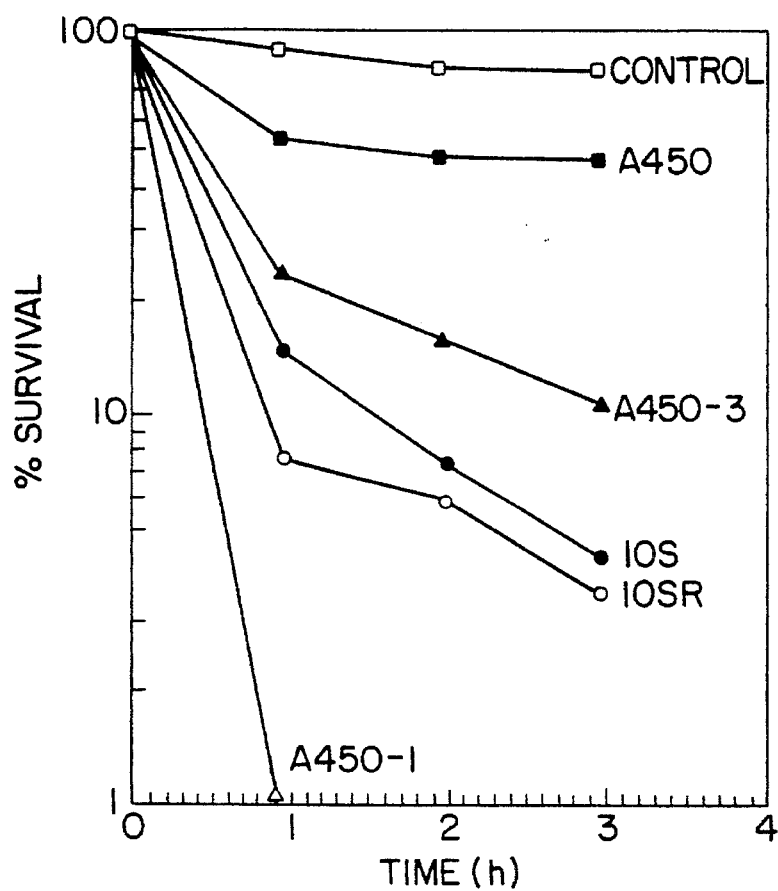
FIG. 6 is a graph showing the serum resistance of A. salmonicida strains.
Figure 7:
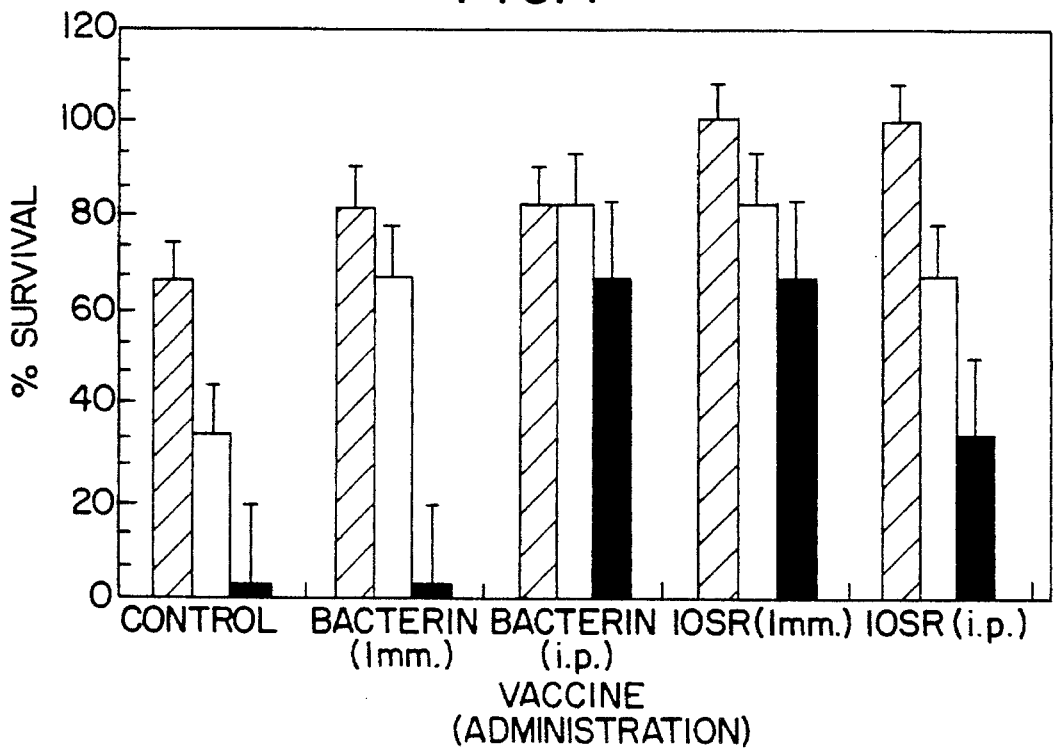
FIG. 7 is a bar graph showing the effectiveness of bacterin and A. salmonicida strain 10SR as vaccines.

Virulent *A. salmonicida* strains are highly resistant to serum killing by the cytolytic action of both immune and non-immune complement. This resistance is due to both LPS and an intact A-layer (Munn et al., 1982). Serum killing experiments revealed that 10S and 10SR were far more sensitive to serum killing than A460. Two strains, A450-3 (the mutant of A450 that is LPS⁺ A-layer) and A450-1 (a mutant of A450 that is LPS⁻ A-layer), were tested for comparison. FIG. 6 is a graph showing the serum resistance of the *A. salmonicida* strains. Values are expressed as percent survival compared to the original viable cell counts. Both 10S and 10SR were more sensitive to serum killing than even A450-3 (A-layer deficient, LPS⁺), in spite of being apparently normal with respect to LPS production and possessing an A-layer, albeit in an altered form in both cases. This suggested that the A-layer in 10S and 10SR was not entirely intact, and that serum complement had access to the cell membrane.

Phenotypic Properties of A-layer Deficient Strains

The growth patterns of strains A450-3 and 10SR-3 are very similar to those of the respective parental strains. Strains A450-3 and 10SR-3 have been demonstrated to be completely avirulent when administered to fish by immersion at a concentration of $2 \times 10^9$ cfu/ml.

Utility of *A. salmonicida* Strain 10S

*A. salmonicida* strain 10S is apparently the first mutant organism to be described which is totally devoid of membrane cytochromes. The organism will therefore serve as a model organism for the study of membrane cytochromes. For example, genes encoding membrane cytochromes may be transformed into *A. salmonicida* strain 10S. The assembly of the membrane cytochromes encoded by these genes may then be analyzed in the absence of interactions with existing membrane cytochromes. The organism will also serve as a suitable model for reconstituting membrane cytochrome complexes and for studying the effects of particular mutations in genes encoding membrane cytochromes.

With particular regard to the present invention, *A. salmonicida* strain 10S is also be useful as a progenitor strain from which strains having the characteristics of *A. salmonicida* 10SR and *A. salmonicida* 10SR-3 may be derived using the techniques described above. Such strains are useful as fish vaccines as described below.

Use of Attenuated *A. salmonicida* Strains as Fish Vaccines

The present inventors have discovered that the attenuated *Aeromonas salmonicida* strain 10SR is effective as a live vaccine. In particular, the susceptibility of a fish to infection by virulent *A. salmonicida* may be reduced when fish are exposed to a vaccine comprising *A. salmonicida* strain 10SR. In a preferred embodiment of this invention, fish may be exposed to the vaccine by immersion in a solution containing a vaccine comprising *A. salmonicida* strain 10SR.

The derivation of 10SR from the wild-type *A. salmonicida* strain A450 via strain 10S involved three separate mutation steps: starting with strain A450, the first mutation step was used to produce the 100 μg/ml streptomycin resistant cells, from which and by means of the second mutation step, the 1 mg/ml streptomycin resistant strain 10S was obtained. The third mutation step was used to produce the streptomycin sensitive revertants strain 10SR from strain 10S. The frequency of obtaining the desired mutant from each of these steps was approximately $1 \times 10^{-7}$. Thus the cumulative frequency of reversion of strain 10SR to the progenitor, virulent strain A450 is theoretically $1 \times 10^{-21}$. No revertants of 10SR were actually obtained in studies designed at recovering such revertants suggesting that the mutation leading from 10S to 10SR is likely to be an essentially irreversible genomic deletion or rearrangement.

Furthermore, it has been found that an A-layer deficient derivative of strain 10SR, strain 10SR-3, is at least equally effective as 10SR as a live vaccine. This finding is contrary to the conventional teachings of the art which suggest that A-layer deficient strains of *A. salmonicida* are ineffective as vaccines. It is further shown that other avirulent A-layer deficient strains of *A. salmonicida*, including A450-3, an avirulent A-layer deficient strain derived directly from the virulent strain A450, are also effective as vaccines. This finding will allow the development of a range of live *A. salmonicida* vaccines based on A-layer deficient strains.

The frequency of mutation to produce A-layer deficient strains is approximately $1 \times 10^{-7}$. Strain 10SR-3 is therefore produced by four successive mutation steps, each occurring with a frequency of approximately $1 \times 10^{-7}$. Thus the cumulative potential frequency of reversion of strain 10SR-3 to the virulent wild-type A450 form is $1 \times 10^{-28}$. A typical vaccine preparation might contain $10^{13}$ cells per liter and thus, a revertant to the virulent strain A450 would therefore be expected to arise once in every $1\times10^{15}$ liters of strain 10SR vaccine. To give some perspective to this number, the estimated volume of the Great Lakes is $2.3\times10^{13}$ liters. While the inventors do not wish to be bound by these theoretical calculations of reversion frequencies, they are presented herein to illustrate the principle that attenuated microorganisms containing multiple mutations are less likely to revert to virulent progenitor forms than attenuated microorganisms containing only a single attenuating mutation.

The following examples are illustrative of the utility of the microorganisms of the present invention as live vaccines.

EXAMPLE I

Comparison of the Efficacy of 10SR as a Live Vaccine and a Bacterin Vaccine

Experiments were performed to compare the efficacy of 10SR as a live vaccine to a commercial bacterin prepared from the wild-type strain A450 (Micrologix Microsal vaccine). The vaccines were administered by both immersion (imm.) and intraperitoneal (i.p.) injection. For injection vaccinations, fish were injected intraperitoneally with $10^7$ 10SR cells or bacterin equivalent (approximately 100 micrograms total antigen) in 0.85% saline solution. Immersion vaccinations were carried out by immersing fish in a solution containing $5\times10^8$ cells/ml of the vaccine strain 10SR (or bacterin equivalent) for 30 minutes. Subsequently, vaccinated and control fish were challenged by immersion exposure to varying concentrations of the highly virulent, heterologous *A. salmonicida* MT26 for 30 minutes. These challenges were carried out 14 days after vaccination. FIG. 7 shows the percentage survival of the fish following challenge with MT26. Challenges were carried out at three concentrations of MT26: $1\times10^6$ CFU/ml (hatched columns), $1\times10^7$ CFU/ml (open columns) and $1\times10^8$ CFU/ml (black columns).

In the control experiments, unvaccinated fish were observed to be killed in proportion to the levels of challenge (the dosage) with MT26. The i.p. injected bacterin protected fish well at all levels of challenge, but when the bacterin was administered by immersion, a dramatic reduction in the level of protection for challenge levels of $10^7$ and $10^8$ cells/ml was observed. Interestingly, 10SR when administered by i.p. injection was not as effective as the bacterin administered by this route, but fish vaccinated by immersion in a 10SR vaccine preparation resisted levels of challenge at least as high as those fish vaccinated by i.p. injection of the bacterin.

$LD_{50}$ values were calculated according to the method of Reed and Meunch (Reed and Meunch, 1938). $LD_{50}$ values and PIs are shown in Table 5.

The data obtained show PI values of approximately 10 and 35 for the vaccination of fish with 10SR by injection or immersion respectively. Thus, 10SR was immunogenic and elicited protective immunity by both methods of administration. The protective immunity conferred by immersion vaccination of 10SR was somewhat more effective than i.p. injection of bacterin. Administration of a vaccine comprising *A. salmonicida* strain 10SR by the more preferred immersion route therefore provides immunity against infection equal or superior to the present state of the art vaccination procedure, that of intraperitoneal injection of bacterin.

TABLE 5

Comparison of the level of immunity induced in rainbow trout by a live furunculosis vaccine vs a bacterin[a]

| Method of Vaccine[b] | administration | $LD_{50}$[c] | PI[d] |
|---|---|---|---|
| None | NA | $3.1 \times 10^6$ | — |
| Bacterin[e] | i.p. injection | $1.0 \times 10^8$ | 32.2 |
|  | immersion | $1.6 \times 10^7$ | 5.2 |
| Live (10SR) | i.p. injection | $3.2 \times 10^7$ | 10.3 |
|  | immersion | $1.1 \times 10^8$ | 35.5 |

[a]Vaccination methods are described in the Materials and methods, the challenge strain used was MT26.
[b]The dosage of vaccine as described in Materials and methods.
[c]Calculated according to the method of Reed and Muench (Reed and Muench, 1938), expressed in cfu/ml.
[d]Protective Index
[e]The bacterin used was a commercially available preparation.

EXAMPLE II

10SR, 10SR-3 and A450-3 as Live Vaccines

Table 6 shows a comparison of the immunity conferred on fish vaccinated with vaccines comprising *A. salmonicida* strains 10SR, 10SR-3 or A450-3. Vaccines were administered by immersion of fish in a solution containing the vaccine at a concentration of $5 \times 10^7$ cfu/ml as described above. Vaccinated fish were challenged by immersion in logarithmic dilutions of *A. salmonicida* MT26 ($10^6$, $10^7$, $10^8$ and $10^9$ CFU/ml). $LD_{50}$ values were calculated based on the survival rates of fish in the various concentrations of challenge strain according to the method of Reed and Meunch (1938). Additionally, experiments were performed to assess the efficacy of providing a second, booster vaccination identical to the first vaccination. Booster vaccinations were administered to fish 14 days after administration of the primary vaccination and fish were challenged 14 days after the booster vaccination.

The results of these experiments are shown in Table 6 below. These experiments demonstrated that the immersion of fish in a vaccine comprising *A. salmonicida* strains 10SR, 10SR-3 or A450-3 is effective in reducing the susceptibility of fish to infection by virulent *A. salmonicida*. The observation that strains 10SR-3 and A450-3 are effective as vaccines contradicts the conventional thinking that *A. salmonicida* vaccines require the presence of the A-layer to be effective. These experiments also show that the susceptibility of the fish to virulent *A. salmonicida* is further reduced by a second immersion in a solution containing the vaccine.

TABLE 6

Efficacy of microorganisms as vaccines administered by immersion of fish.

| Vaccination (by immersion) | | None (control) | 10SR | 10SR-3 | A450-3 |
|---|---|---|---|---|---|
| | | Vaccine Type | | | |
| Single | [a]$LD_{50}$ | $1.3 \times 10^6$ | $2.8 \times 10^7$ | $4 \times 10^7$ | $3.3 \times 10^7$ |
| | [b]PI | — | 21.5 | 30.8 | 25.4 |
| Double | [a]$LD_{50}$ | $3.3 \times 10^6$ | $1 \times 10^9$ | $2.5 \times 10^9$ | $1 \times 10^9$ |
| | [b]PI | — | 303.0 | 757.6 | 303.0 |

[a] = $LD_{50}$ in cfu/ml of MT26
[b] = Protective index

EXAMPLE III

Effects of Varying Microorganism Concentration on Vaccine Efficacy

Experiments were performed to assess the effect of varying the concentration of the microorganisms in the vaccine solution. For these tests, *A. salmonicida* strain OSR-3 was selected. The vaccine was administered by immersion and vaccinated fish were challenged with *A. salmonicida* strain MT26. Two concentrations of the microorganism were tested; $1 \times 10^7$ CFU/ml and $1 \times 10^8$ CFU/ml. An identical booster immersion was provided 14 days following the primary vaccination. As described in Example II, the vaccinated fish were exposed to a range of concentrations of *A. salmonicida* strain MT26 from $10^6$ to $10^9$ CFU/ml and the method of Reed and Meunch (1938) was used to calculate $LD_{50}$ values. The results are shown in Table 7.

TABLE 7

Comparative efficacy of vaccine concentrations.

| | Control (non-vaccinated) | Concentration of 10SR-3: $1 \times 10^7$ cfu/ml | $1 \times 10^8$ cfu/ml |
|---|---|---|---|
| [a]$LD_{50}$ | $1.9 \times 10^5$ | $4.1 \times 10^7$ | $3.7 \times 10^8$ |
| [b]PI | — | 215.8 | 1947.4 |

[a]In cfu/ml
[b]Protective index.

Thus, higher concentrations of the microorganism in the live vaccine produces a higher PI value and therefore affords a greater degree of protection to a vaccinated fish population.

EXAMPLE IV

Production of Other *A. salmonicida* Strains Useful as Live, Attenuated Vaccines Having herein provided methods by which the microorganism strains of the present invention were isolated, it will be readily apparent to one skilled in the art that other microorganism strains, sharing the identifying characteristics of the microorganism strains of the present invention may now be isolated. Such microorganism strains are also encompassed in the present invention.

Thus, attenuated strains of *A. salmonicida* useful as live vaccines (which are herein referred to as attenuated vaccine strains of *A. salmonicida*) may be obtained by a process selected from the processes in (a), (b) or (c) below:

(a) a process comprising a first step of culturing a virulent progenitor strain of *Aeromonas salmonicida* in the presence of an aminoglycoside antibiotic at a level of 10 μg–100 μg antibiotic per milliliter of culture to produce a first aminoglycoside antibiotic resistant, attenuated strain;

a second step of culturing the first aminoglycoside antibiotic resistant attenuated strain in the presence of an aminoglycoside antibiotic at a level of 100 μg–2000 μg antibiotic per milliliter of culture to produce a second aminoglycoside antibiotic resistant, attenuated strain which strain is membrane cytochrome negative;

a third step of culturing the second aminoglycoside antibiotic resistant, membrane cytochrome negative, attenuated strain in the absence of aminoglycoside antibiotic to produce the attenuated vaccine strain which is a revertant aminoglycoside antibiotic sensitive, membrane cytochrome positive, attenuated strain;

(b) a process comprising a first step of culturing a virulent progenitor strain of *Aeromonas salmonicida* in the presence of an aminoglycoside antibiotic at a level of 10 μg–100 μg antibiotic per milliliter of culture to produce a first aminoglycoside antibiotic resistant, attenuated strain;

a second step of culturing the first aminoglycoside antibiotic resistant attenuated strain in the presence of an aminoglycoside antibiotic at a level of 100 μg–2000 μg antibiotic per milliliter of culture to produce a second aminoglycoside antibiotic resistant, attenuated strain which strain is membrane cytochrome negative;

a third step of culturing the second aminoglycoside antibiotic resistant, membrane cytochrome negative, attenuated strain in the absence of aminoglycoside antibiotic to produce the revertant aminoglycoside antibiotic sensitive, membrane cytochrome positive, attenuated strain;

a fourth step of culturing the revertant, aminoglycoside antibiotic sensitive, membrane cytochrome positive, attenuated strain at a temperature of between 25° C. and 37° C. to produce the attenuated vaccine strain which is a revertant, aminoglycoside antibiotic sensitive, membrane cytochrome positive, attenuated strain that lacks an A-layer;

(c) a process comprising culturing a virulent *Aeromonas salmonicida* strain at a temperature of between 25° C. and 37° C. to produce an attenuated vaccine strain that lacks an A-layer.

The identification of A-layer deficient strains may be achieved by growing the microorganisms on Congo Red agar as described above. A-layer deficient mutants lack the ability to take up the Congo Red dye and appear as white colonies among the red A-layer possessing colonies. A-layer deficiency may be verified by electron microscopy and SDS-PAGE as described above.

Suitable aminoglycoside antibiotics include, but are not limited to streptomycin, kanamycin, gentamicin and netilmicin. In a preferred embodiment of the present invention, the aminoglycoside antibiotic of choice is streptomycin.

An attenuated strain obtained by the methods of the present invention as outlined above is then assessed for utility as a live, attenuated vaccine, suitable for administration by immersion of fish in a solution containing the vaccine. This assessment is made by immersing fish in a solution containing the vaccine and subsequently exposing the vaccinated fish to a virulent strain of *A. salmonicida* such as strain MT26 as described above. A particular microorganism is suitable for use as a live attenuated vaccine if it is capable of reducing the susceptibility of fish vaccinated with the microorganism. As described above and in Example VI below, variations in the conditions of immersion (concentration of microorganism, length of time of immersion, number of times of immersion) will alter the efficacy of a particular microorganism as a live vaccine. In preferred embodiments, the reduction in susceptibility produced by immersion vaccination of fish with a particular microorganism obtained by the methods of the present invention will be equated to a PI of at least 20, and in preferred embodiments, to a PI of at least 100.

The scope of this invention additionally encompasses microorganisms that are mutants of *Aeromonas salmonicida* strains 10SR, 10SR-3 and A450-3 and of microorganisms produced according to the methods of the present invention where such microorganisms are useful as live, attenuated vaccines. Such mutants will retain the capability of inducing protective immunity against virulent *A. salmonicida* in a susceptible fish, but may be altered in other characteristics. Thus, such mutants might have altered growth characteristics including the ability to utilize particular energy sources, altered growth rates under particular conditions or may have sustained further attenuating mutations, reducing still further the possibility of reversion to a virulent form. Such changes in characteristics may be effected by the introduction of heterologous genes into the microorganisms by methods including, but not limited to, transformation, plasmid conjugation and viral transfection.

Alternatively, the changes may be effected by the selection of spontaneous mutant forms or by selection of induced mutant forms, induced by the application of mutagenic agents such as ultraviolet light. Such mutagenesis techniques are well known in the art and are described in numerous publications including Sambrook et al. (1989).

Illustrative of such mutant microorganisms is a microorganism produced by inserting a gene encoding an antigenic protein produced by a fish pathogen other than *A. salmonicida* into the A-protein gene of *A. salmonicida* strain 10SR. Such gene insertion can be achieved by homologous recombination. Insertion of the foreign antigen gene into the A-protein gene serves three purposes:

1. Disruption of the A-protein gene (to cause the strain to become A-layer deficient) and therefore a possible enhancement of the efficacy of the strain as a live vaccine for protection against *A. salmonicida* infection.

2. Expression of an antigen from a second fish pathogen, such that the vaccine will now reduce the susceptibility of vaccinated fish to two fish pathogens.

3. Avoidance of potential disruption of the growth characteristics of the progenitor 10SR strain resulting from random insertion of foreign genetic materials.

Suitable candidate genes for this approach include surface antigen genes from bacterial fish pathogens such as species of Vibrio (such as *V. anguillarum*), Yersinia and Flavobacterium and coat protein genes from fish pathogenic viruses such as Infectious Hematopoietic Necrosis Virus (IHNV) and Infectious Pancreatic Necrosis Virus (IPNV).

EXAMPLE V

Formulation of Live Vaccines

The microorganisms of the present invention may be included in live vaccine preparations for vaccination of fish.

These vaccines are administered by exposing a fish to the vaccine. The step of exposing the fish to the vaccine is selected from a number of methods, including immersing the fish in a solution of the vaccine, spraying the fish with a solution of the vaccine, adding the vaccine to food provided to the fish and intraperitoneal injection. In a preferred embodiment, the fish are exposed to the vaccine by immersion in a solution containing the vaccine.

A live vaccine comprising microorganisms of the present invention is produced by growing the microorganisms in culture, harvesting them and packaging the microorganisms for use as a vaccine. Such vaccine preparations may be produced and formulated as described below:

The microorganism strain is isolated according to the methods of the present invention or is obtained from the inventors or from the American Type Culture Collection by the accession numbers given above.

A number of methods may be used to assess the purity of cultures throughout the process of growing the microorganism and preparing the vaccine. These include:

1. Microscopic observation. The characteristic colonial mythology of these microorganisms on TSA is hockey puck-type colonies, slightly raised and confined with circular, regular colony margins. The colonies are a creamy brown with a brown diffusible pigment.

2. Agglutination with specific polyvalent *A. salmonicida* rabbit antiserum.

3. Microscopic observation of the microorganisms. *A. salmonicida* are typically gram negative, non-motile rods, usually clumped together. Strains 10S, 10SR and 10SR-3 described in the present invention are much smaller than the wild-type strands of *A. salmonicida*, and are almost coccal in shape and appearance.

4. Other methods. Gel electrophoresis of cell extract to characterize outer membrane proteins may be utilized as described above to distinguish between the strains of the present invention.

A number of culture media may be used to propagate and produce strands of the present invention including TSA, casein digest medium (SCDM) and LB-Davis+0.2% glucose.

Several methods may be used to maintain the strains of the present invention. For example, the strains may be grown to mid-log phase in LB-Davis+0.2% glucose for 18–24 hours at 18°–23° C. Thereafter, portions of the culture (generally less than 20 ml) are aseptically transferred to vials, glycerin is added to 15% volume and the vials are frozen at −20° C. or below. Alternatively, subcultures of the strains may be inoculated onto TSA slants, incubated at 18°–23° C. for 18–24 hours and freeze dried.

Large quantities of the strains may be grown and harvested using standard microbiological methods. The following example is illustrative only of the general principle. Approximately 50 ml of broth media is inoculated with 0.1 ml of the frozen preserved culture or freeze-dried inocula and incubated for 18–24 for 18°–23° C. with shaking at 250 rpm. Alternatively, a single colony from a TSA plate can be used to seed the broth. This broth is then used to inoculate 250 ml of the same media which is incubated under the same conditions for 18–24 hours. The 250 ml culture is grown to at least 5 O.D units/ml measured at 650 nm (equivalent to approximately $2\times10^9$ CFU/ml). The 250 ml culture is then used to inoculate a large volume of the media in a fermentor. The fermentor media is inoculated by pumping the 250 ml culture into the fermentor through a steam sterilized line. Suitable fermentors include the 30 liter ChemAp fermentor and the 140 liter LH Model 3000-Series 1 fermentor. In the fermentor, the production culture is aerated at 60–80 L/minute. Stirring varies from 200–800 rpm. The pH is maintained at 7.0. Temperature is maintained at 18°–23° C. Foaming may be controlled by a mechanical foam breaker and/or by the automatic addition of sterile propylene glycol (PPG). The growth of the culture in the fermentor is determined spectrophotometrically. For an acceptable yield, the optical density should be at least 5 OD units/ml at 650 nm prior to harvesting. No more than 36 hours is allowed to pass between the time of inoculation of the fermentor and the time of harvesting.

When bacterial biomass conforms to specifications, a sample is removed for purity testing by standard methods. For example, axenic growth is confirmed by streaking samples from the fermentor onto two TSA plates and incubating the plates at about approximately 20° C. (room temperature) and 35°–37° C. for at least 48 hours. Plates are then inspected for the presence of contaminating colonies.

The material is harvested from the fermentor by aseptically pumping the mixture from the fermentor into presterilized containers containing 15% by volume of sterile glycerin. The glycerin is present to preserve viability of the microorganisms, particularly when the vaccine is subsequently frozen and thawed. Other suitable preservatives, for example trehalose, dimethylsulphoxide or sucrose, may be substituted for the glycerin. The vaccine preparation is then frozen at −20° C. or below. Typically, the vaccine is packaged in 100 ml, 1 liter or 4 liter containers. Such containers are suitable for administering the vaccine to fish.

Prior to use, the vaccine preparation is thawed and appropriate amounts are added to the volume of water in which the fish are to be immersed.

The safety of particular vaccine preparations may be assessed as follows: a minimum of 30 salmonids are immersed in a 1:100 dilution of the vaccine (equivalent to approximately $10^7$ microorganisms/ml) for 20 minutes. Seven to ten days later, they are reimmunized by repeating this procedure. Fish are then placed into holding tanks where they are observed for at least 14 days in order to determine whether any fatalities arise as a result of the vaccination procedure. Greater than 90% of the fish must be alive and showing no signs of disease after seven days. If greater than 10% of the fish die to causes attributable to the vaccination procedure, then the vaccine is unsatisfactory.

The potency of vaccine preparations produced according to this invention may be assessed as described above. Briefly, three groups of seven to ten fish each are challenged at least 14 days after being immunized with the vaccine preparation by being immersed in a range of dilutions of the virulent *A. salmonicida* strain MT26. Preliminary challenges are run on non-vaccinated fish to determine the optimum challenge conditions. Seven to ten fish are exposed to each of the three levels of the virulent organism, ranging from $10^6$ to $10^8$ CFU/ml for a minimum of 20 minutes. The identical procedure is performed with non-immunized control fish. The fish are observed for a minimum of 14 days post challenge and the cause of mortality determined. In preferred embodiments of the present invention, the reduction in susceptibility of exposed fish correlating with the administration of vaccine equates to a protective index of at least 20 and more preferable to a protective index of at least 100.

EXAMPLE VI

Administration of Live Vaccines by Immersion

Three main parameters may be varied when exposing fish by immersion to the vaccines of the present invention. These three parameters are the concentration of the vaccine solution (i.e. the amount of the vaccine in a given volume of water), the length of time of immersion and the number of times of immersion. Generally, increasing any or all of these three parameters will provide increased protection against infection by virulent *A. salmonicida* strains. The efficacy of a particular combination of these parameters may be determined by the methods described above whereby fish are immersed in the vaccine and subsequently exposed to the pathogenic *A. salmonicida* strain MT26. The efficacy may be expressed as a Protective Index (PI) value and the efficacy of a particular combination of conditions may be compared to that of another combination of conditions by comparing the PI value for each combination. A higher PI value equates to a greater reduction in susceptibility of vaccinated fish to infection.

Any amount of exposure of fish to the vaccine that results in uptake of the vaccine by the fish will result in some reduction in the susceptibility of the fish to infection by virulent *A. salmonicida*; the extent of the reduction may readily be assessed by determination of PI values or determination and comparison of $LD_{50}$ values, as described above and using the aforementioned methods. Determination of the sufficiency of the parameters of a particular immersion regime—concentration of the vaccine solution (i.e. the amount of the vaccine in a given volume of water), the length of time of immersion and the number of times of immersion—may be determined using these methods. In addition, the effect of varying a single parameter may be determined by maintaining other parameters constant and determining the reduction in susceptibility conferred by varying the single parameter.

In a preferred embodiment of the present invention, the vaccine is administered by at least a single immersion of fish in a solution containing at least $10^6$ cells/ml of the live, attenuated microorganism strain for at least 15 minutes. In more preferred embodiments of the present invention, the vaccine is administered by immersion as described in Examples I–III, wherein fish are immersed, preferably at least twice, in a solution of the vaccine containing at least $10^7$ and preferably at least $10^8$ cells/ml of the live attenuated microorganism for at least 30 minutes.

The present invention relates primarily to live attenuated vaccines which confer protection against furunculosis caused by *A. salmonicida*. It should be noted that this does not preclude use of the vaccines for protection against other fish diseases against which the vaccines are effective. Other diseases which may be protected against by the vaccines of this invention include vibriosis (Norqvist et el., 1989)

Having illustrated and described the principles of obtaining and using the attenuated microorganisms, it will be apparent to one skilled in the art that the invention can be modified in arrangement and detail without departing from such principles. We claim all modifications coming within the spirit and scope of the claims presented herein.

BIBLIOGRAPHY

Ames (1974). *J. Biol. Chem.* 249:634–44.
Belland and Trust (1988). *J. Bacteriol.* 163:871–81.
Bolin et al. (1985). *Infect. Immun.* 48:234–40.
Borghouthi et al. (1989). *J. Bacteriol* 171:1811–16.
Bott et al. (1990). *Molec. Microbiol.* 4:200, 2147–2157.
Brown et al. (1987). *J. Infect. Dis.* 166:86–92.
Brubaker and Surgella (1962). *J. Bacteriol.* 84:615–24.
Chart et al. (1984). *J. Bacteriol.* 158:16–22.
Chart and Trust (1983). *J. Bacteriol.* 156:758–64.
Cipriano and Starliper (1982). *Prog. Fish-Cult.* 44:167–9.
Curtis and Kelly (1987). *Infect Immun.* 66:3036–43.
Darveau et al. (1983). *J. Bacteriol.* 156:1006–11.
DeMay and Moeremans (1986). *In Advanced techniques in biological electron microscopy,* 229–71, Koehler JK (ed.), Springer-Verlag, Berlin.
Dooley et al. (1989). *J. Bacteriol.* 171:190–7.
Duff (1942). *J. Immunol.* 44:87–94.
Ellis et al. (1981). *J. Fish Dis.* 4:41–51.
Ellis et al. (1988). *J. Fish Dis.* 11:309–323.
Filip et al. (1973). *J. Bacteriol.* 115:717–22.
Grieco (1982). *Antimicrobial Therapy* 66:32–7.
Hoiseth and Stocker (1981). *Nature* 291:238–239.
Johnson and Amend (1984). *J. Fish Dis.* 7:101–5.
Kay et al. (1981). *J. Bacteriol.* 147:1077–84.
Kay et al. (1984). *Can. J. Biochem. Cell Biol.* 62:1064–71.
Kay et al. (1986). *In Pathology in Marine Aquaculture,* 217–229, Vivares et al. (eds.), European Aquaculture Society, Special Publication No. 9, Bredene, Belgium.
Kay and Trust (1991). *Experientia* 47:412–16.
Klontz and Anderson (1970). In *A symposium on diseases of fishes and shellfishes,* 16–20, Snieszko SF (ed.), American Fish Society, Washington D.C.
Lee and Ellis (1989). *FFMS Microbiol. Lett.* 61:127–32.
Lee and Ellis (1990). *J. Bacteriol.* 172:5382–93.
McCarthy et al. (1983). *J. Fish Dis.* 6:155–74.
Markwell et al. (1978). *Anal. Biochem.* 87:206–10.
Munn et al. (1982). *Infect. Immun.* 36:1069–75.
Newman and Majnarich (1985). *Fish Pathol.* 20:403–11.
Norqvist et al. (1989). *Appl. Env. Microbiol.* 55:1400–5.
Olivier et al. (1985). *J. Fish Dis.* 8:43–55.
Paterson and Fryer (1974). *J. Fish Reg. Board Can.* 31:1751–5.
Reed and Muench (1938). J. Hyg. 27:493–7.
Sambrook et al. (1989). *Molecular Cloning,* 2nd. ed. Cold Spring Harbor Laboratory, Cold Spring Harbor, N.Y.
Schwyn and Neilands (1987). *Anal. Biochem.* 160:47–66.
Shieh and Maclean (1976). *Int. J. Biochem.* 653–6.
Sigwart et al. (1989). *Infect. Immun.* 57:1858–1861.
Singer et al. (1991). *J. of Microbiol. Methods* 13:49–60.
Smith (1990). *J. Gen Microbiol.* 136:377–83.
Somers et al. (1981). *Mol. Gen. Genet.* 181:338–45.
Tatner (1987). *Aquaculture* 62:173–85.
Towbin et al. (1979). *Proc. Natl. Acad. Sci. USA* 74:4350–4.
Trust (1986). *Annu. Rev. Microbiol.* 40:479–502.
Trust et al. (1982). In *Developmental and Comparative Immunology,* 175–180, Pergamon Press Ltd. (eds.), USA.
Trust et al. (1983). *J. World Maricul. Soc.* 14:193–200.
Tsai and Frasch (1982). *Anal. Biochem.* 110:115–19.
Vaughan et al. (1990). *Res. Microbiol.* 141:941–3.
Willis et al. (1974). *Arch. Biochem. Biophys.* 161:64–75.
Wood et al. (1986). *Antimicrobial Agents and Chemotherapy* 29:992–6.
Wray et al. (1977). *J. Hyg.* 79:17–24.

We claim:

1. A live vaccine for the immunization of fish wherein the vaccine comprises live microorganisms selected from the group consisting of: *Aeromonas salmonicida* strain 10SR or mutants thereof that are capable of inducing protective immunity in a susceptible fish against infection by virulent *Aeromonas salmonicida; Aeromonas salmonicida* strain 10SR-3 or mutants thereof that are capable of inducing protective immunity in a susceptible fish against infection by virulent *Aeromonas salmonicida*; and *Aeromonas salmonicida* strain A450-3 or mutants thereof that are capable of inducing protective immunity against infection by virulent *Aeromonas salmonicida* in susceptible fish.

2. The live vaccine of claim 1, wherein the vaccine is capable of inducing protective immunity against infection by virulent *Aeromonas salmonicida* in a susceptible fish when administered by immersion of the fish for a sufficient number of times in a solution containing a sufficient amount of the live vaccine for a sufficient period of time to reduce the susceptibility of the fish to infection by virulent *Aeromonas salmonicida*.

3. A method of reducing the susceptibility of fish to infection by virulent strains of *Aeromonas salmonicida* wherein the method comprises exposing fish to a sufficient amount of the live vaccine of claim 1 so as to reduce the susceptibility of the fish to infection by virulent *Aeromonas salmonicida*.

4. The method of claim 3 wherein the exposing step comprises immersing the fish for a sufficient number of times in a solution containing a sufficient amount of the live vaccine for a sufficient period of time to reduce the susceptibility of the fish to infection by virulent *Aeromonas salmonicida*.

5. The method of claim 4 wherein the exposing step provides a Protective Index greater than 20 in the fish immersed in the solution.

6. The method of claim 4 wherein the exposing step provides a Protective Index of greater than 100 in susceptible fish immersed in the solution.

7. The method of claim 4 wherein the exposing step comprises immersing the fish twice in the solution containing the sufficient amount of the live vaccine for the sufficient period of time to reduce the susceptibility of the fish to infection by virulent *Aeromonas salmonicida*.

8. The method of claim 7 wherein the exposing step provides a Protective Index of greater than 100 in susceptible fish immersed in the solution.

9. The method of claim 3 wherein the exposing step comprises intraperitoneal injection of the vaccine into the fish.

10. A live vaccine for the immunization of fish wherein the live vaccine comprises an attenuated strain of *Aeromonas salmonicida* wherein said strain does not possess an A-layer.

11. The live vaccine of claim 10 wherein the vaccine comprises the live vaccine in a container with a preservative suitable for maintaining the viability of the live vaccine.

12. The live vaccine of claim 10 wherein the vaccine is capable of reducing the susceptibility of a susceptible fish to infection by virulent *Aeromonas salmonicida* when the fish is exposed to the vaccine by immersion of the fish for a sufficient number of times in a solution containing a sufficient amount of the live vaccine for a sufficient period of time to reduce the susceptibility of the fish to infection by virulent *Aeromonas salmonicida*.

13. The live vaccine of claim 12 wherein the vaccine produces a protective index of greater than 100 when susceptible fish are twice immersed in a solution of the vaccine for a period of 30 minutes, said immersions being 14 days apart and said solution containing $5 \times 10^8$ cells/ml of the microorganisms comprising the vaccine.

14. A method of reducing the susceptibility of fish to infection by virulent strains of *Aeromonas salmonicida* wherein the method comprises exposing fish to a sufficient amount of the vaccine of claim 10 so as to reduce the susceptibility of the fish to infection by virulent *Aeromonas salmonicida*.

15. A live vaccine for the immunization of fish wherein the vaccine comprises *Aeromonas salmonicida* strain 10SR or mutants thereof that are capable of inducing protective immunity in a susceptible fish against infection by virulent *Aeromonas salmonicida*.

16. A method of reducing the susceptibility of a fish to infection by virulent strains of *Aeromonas salmonicida* wherein the method comprises exposing the fish to a sufficient amount of the live vaccine of claim 15 to reduce the susceptibility of the fish to infection by virulent *Aeromonas salmonicida*.

17. A live vaccine for the immunization of fish wherein the vaccine comprising *Aeromonas salmonicida* strain 10SR-3 or mutants thereof that are capable of inducing protective immunity against infection By virulent *Aeromonas salmonicida* in susceptible fish.

18. A method of reducing the susceptibility of a fish to infection by virulent strains of *Aeromonas salmonicida* wherein the method comprises exposing the fish to a sufficient amount of the live vaccine of claim 17 to reduce the susceptibility of the fish to infection by virulent *Aeromonas salmonicida*.

19. A live vaccine for the immunization of fish wherein the vaccine comprises *Aeromonas salmonicida* strain A450-3 or mutants thereof that are capable of inducing protective immunity against infection by virulent *Aeromonas salmonicida* in susceptible fish.

20. A method of reducing the susceptibility of a fish to infection by virulent strains of *Aeromonas salmonicida* wherein the method comprises exposing the fish to a sufficient amount of the live vaccine of claim 19 to reduce the susceptibility of the fish to infection by virulent *Aeromonas salmonicida*.

21. An attenuated *Aeromonas salmonicida* microorganism selected from the group consisting of: *Aeromonas salmonicida* strain 10S; *Aeromonas salmonicida* strain 10SR; and *Aeromonas salmonicida* strain 10SR-3.

22. The microorganism of claim 21 wherein said microorganism is present in a biologically pure culture.

23. The microorganism of claim 21 wherein the microorganism is *Aeromonas salmonicida* strain 10S.

24. The microorganism of claim 21 wherein the microorganism is *Aeromonas salmonicida* strain 10SR.

25. The microorganism of claim 21 wherein the microorganism is *Aeromonas salmonicida* strain 10SR-3.

26. A live vaccine for the immunization of fish wherein the vaccine comprises microorganisms selected from the group consisting of *Aeromonas salmonicida* 10SR, *Aeromonas salmonicida* 10SR-3 and *Aeromonas salmonicida* A450-3.

27. The vaccine of claim 26 wherein the vaccine comprises *Aeromonas salmonicida* 10SR.

28. The vaccine of claim 26 wherein the vaccine comprises *Aeromonas salmonicida* 10SR-3.

29. The vaccine of claim 26 wherein the vaccine comprises *Aeromonas salmonicida* A450-3.

30. A method of reducing the susceptibility of a fish to infection by a virulent strain of *Aeromonas salmonicida* wherein the method comprises immersing the fish in a solution of the vaccine according to claim 26.

31. The method of claim 30 wherein the method comprises immersing the fish for a sufficient number of times in a solution containing a sufficient amount of the vaccine for a sufficient period of time to reduce the susceptibility of the fish to infection by the virulent strain of *Aeromonas salmonicida*.

32. The method of claim 14 wherein the exposing step comprises immersing the fish for a sufficient number of times in a solution containing a sufficient amount of the live vaccine for a sufficient period of time to reduce the susceptibility of the fish to infection by virulent *Aeromonas salmonicida*.

33. The method of claim 32 wherein the exposing step comprises immersing the fish twice in the solution containing the sufficient amount of the live vaccine for the sufficient period of time to reduce the susceptibility of the fish to infection by virulent *Aeromonas salmonicida*.

34. The method of claim 14 wherein the exposing step comprises intraperitoneal injection of the vaccine into the fish.

* * * * *